US010987026B2

(12) United States Patent
Shetty et al.

(10) Patent No.: US 10,987,026 B2
(45) Date of Patent: Apr. 27, 2021

(54) CAPNOGRAPHY MODULE WITH AUTOMATIC SWITCHING BETWEEN MAINSTREAM AND SIDESTREAM MONITORING

(71) Applicant: Spacelabs Healthcare LLC, Snoqualmie, WA (US)

(72) Inventors: Nityanand Shetty, Secunderabad (IN); Rajanala Venkata Subrahmanyam, Hyderabad (IN); Bottu V. Satishkumar, Visakhapatnam (IN); Imandi Shiv Kiran, Kakinada (IN); Katherine Stankus, Woodinville, WA (US)

(73) Assignee: Spacelabs Healthcare LLC, Snoqualmie, WA (US)

( * ) Notice: Subject to any disclaimer, the term of this patent is extended or adjusted under 35 U.S.C. 154(b) by 1587 days.

(21) Appl. No.: 14/289,833

(22) Filed: May 29, 2014

(65) Prior Publication Data
US 2015/0018703 A1   Jan. 15, 2015

Related U.S. Application Data

(60) Provisional application No. 61/829,222, filed on May 30, 2013.

(51) Int. Cl.
*A61B 5/097* (2006.01)
*A61M 16/01* (2006.01)
(Continued)

(52) U.S. Cl.
CPC ............ *A61B 5/097* (2013.01); *A61B 5/0836* (2013.01); *A61B 5/7435* (2013.01); *A61M 16/01* (2013.01);
(Continued)

(58) Field of Classification Search
CPC ..... A61B 5/0836; A61B 5/097; A61M 16/085
See application file for complete search history.

(56) References Cited

U.S. PATENT DOCUMENTS

| 2,003,120 A | 5/1935 | Penniman |
| 2,004,116 A | 6/1935 | Jennings |

(Continued)

FOREIGN PATENT DOCUMENTS

| CN | 1293943 | 5/2001 |
| CN | 1348740 | 5/2002 |

(Continued)

OTHER PUBLICATIONS

Kevin James: "Status Checks", PC Interfacing and Data Acquisition: Techniques for Measurement, Instrumentation and Control, Jul. 17, 2000, pp. 66-67, XP055461225, ISBN:978-0-7506-4624-6.

(Continued)

*Primary Examiner* — Rajeev P Siripurapu
*Assistant Examiner* — Michael A Catina
(74) *Attorney, Agent, or Firm* — Novel IP

(57) ABSTRACT

A capnography module for a patient monitoring system includes a hardware switching mechanism and a software mechanism for switching the capnography module automatically between a mainstream monitoring mode and a sidestream monitoring mode. The hardware switching mechanism along with software detection is capable of detecting the connection of a mainstream capnography sensor and a sidestream sampling line and generates flags to notify the software switching mechanism which sensor or line is connected. The software switching mechanism notifies a controller board in the module which monitoring system is available and the controller board operates the module in the respective mode. The capnography module also includes a connector latching mechanism for securing
(Continued)

the mainstream capnography sensor to the module and preventing accidental disconnection.

17 Claims, 9 Drawing Sheets

(51) Int. Cl.
    *G01N 33/00*     (2006.01)
    *A61B 5/00*     (2006.01)
    *A61M 16/00*     (2006.01)
    *A61M 16/08*     (2006.01)
    *A61B 5/083*     (2006.01)
    *G01N 33/497*     (2006.01)

(52) U.S. Cl.
    CPC ........ *A61M 16/021* (2017.08); *A61M 16/085* (2014.02); *G01N 33/004* (2013.01); *A61M 2205/502* (2013.01); *A61M 2230/42* (2013.01); *A61M 2230/432* (2013.01); *G01N 33/497* (2013.01)

(56) References Cited

U.S. PATENT DOCUMENTS

| | | |
|---|---|---|
| 2,005,005 A | 6/1935 | Preston |
| 2,005,146 A | 6/1935 | Kotrbaty |
| 2,006,213 A | 6/1935 | Halliday |
| 2,007,120 A | 7/1935 | Holmes |
| 2,008,221 A | 7/1935 | Molander |
| 2,008,251 A | 7/1935 | Hillebrand |
| 2,009,121 A | 7/1935 | Price |
| 2,009,326 A | 7/1935 | Sanchez-Vello |
| 2,246,464 A | 6/1941 | Gerber |
| 2,808,580 A | 10/1957 | Fuller |
| 2,820,651 A | 1/1958 | Phillips |
| 2,912,858 A | 11/1959 | Fuller |
| 2,944,547 A | 7/1960 | Ziherl |
| 3,517,639 A | 6/1970 | Whitsel |
| 3,608,545 A | 9/1971 | Novack |
| 3,618,592 A | 11/1971 | Stewart |
| 3,673,863 A | 7/1972 | Spacek |
| 3,689,908 A | 9/1972 | Ray |
| 3,733,482 A | 5/1973 | Miller |
| 3,757,577 A | 9/1973 | Bozek |
| 3,844,171 A | 10/1974 | Rodger |
| 3,897,606 A | 8/1975 | Schleining |
| 3,938,551 A | 2/1976 | Henkin |
| 3,954,010 A | 5/1976 | Hilblom |
| 3,981,329 A | 9/1976 | Wohlwend |
| 4,064,826 A | 12/1977 | Pauli |
| 4,148,312 A | 4/1979 | Bird |
| 4,167,115 A | 9/1979 | Stoever |
| 4,323,064 A | 4/1982 | Hoenig |
| 4,428,230 A | 1/1984 | Testone |
| 4,428,507 A | 1/1984 | Sneider |
| 4,513,294 A | 4/1985 | Anderson |
| 4,557,216 A | 12/1985 | Demyon |
| 4,615,547 A | 10/1986 | Sutcliffe |
| 4,625,731 A | 12/1986 | Quedens |
| 4,630,485 A | 12/1986 | Wastl, Sr. |
| 4,630,486 A | 12/1986 | Miles |
| 4,643,693 A | 2/1987 | Rubinstein |
| 4,697,450 A | 10/1987 | Bachman |
| 4,869,253 A | 9/1989 | Craig |
| 4,879,997 A | 11/1989 | Bickford |
| 4,899,585 A | 2/1990 | Kulha |
| 4,903,222 A | 2/1990 | Carter |
| 4,944,305 A | 7/1990 | Takatsu |
| 4,989,791 A | 2/1991 | Ridenour |
| 4,991,576 A | 2/1991 | Henkin |
| 4,993,683 A | 2/1991 | Kreuzer |
| 5,086,397 A | 2/1992 | Schuster |
| 5,087,906 A | 2/1992 | Eaton |
| 5,101,851 A | 4/1992 | Abadi |
| 5,144,898 A | 9/1992 | Posly |
| 5,174,163 A | 12/1992 | Gussman |
| 5,197,480 A | 3/1993 | Gebhardt |
| 5,213,108 A | 5/1993 | Bredesen |
| 5,222,486 A | 6/1993 | Vaughn |
| 5,231,981 A | 8/1993 | Schreiber |
| 5,233,975 A | 8/1993 | Choate |
| 5,253,641 A | 10/1993 | Choate |
| 5,262,944 A | 11/1993 | Weisner |
| 5,291,182 A | 3/1994 | Wiseman |
| 5,292,564 A | 3/1994 | Lee |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,333,106 A | 7/1994 | Lanpher |
| 5,339,826 A | 8/1994 | Schmidt |
| 5,348,008 A | 9/1994 | Bornn |
| 5,372,389 A | 12/1994 | Tam |
| 5,373,746 A | 12/1994 | Bloss |
| 5,375,604 A | 12/1994 | Kelly |
| 5,377,399 A | 1/1995 | Ogawa |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,520,191 A | 5/1996 | Karlsson |
| 5,537,992 A | 7/1996 | Bjoernstijerna |
| 5,553,296 A | 9/1996 | Forrest |
| 5,558,418 A | 9/1996 | Lambright |
| 5,563,495 A | 10/1996 | Tomiyori |
| 5,584,291 A | 12/1996 | Vapola |
| 5,586,909 A | 12/1996 | Saba |
| 5,603,330 A | 2/1997 | Suga |
| 5,633,457 A | 5/1997 | Kilar |
| 5,682,526 A | 10/1997 | Smokoff |
| 5,684,504 A | 11/1997 | Verhulst |
| 5,687,717 A | 11/1997 | Halpern |
| 5,692,494 A | 12/1997 | Pernetti |
| 5,715,813 A | 2/1998 | Guevrekian |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,752,917 A | 5/1998 | Fuchs |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,800,387 A | 9/1998 | Duffy |
| 5,819,741 A | 10/1998 | Karlsson |
| 5,852,440 A | 12/1998 | Grossman |
| 5,855,550 A | 1/1999 | Lai |
| 5,868,133 A | 2/1999 | DeVries |
| 5,904,328 A | 5/1999 | Leveridge |
| 5,947,907 A | 9/1999 | Duich |
| 5,956,013 A | 9/1999 | Raj |
| 5,966,760 A | 10/1999 | Gallant |
| 5,975,081 A | 11/1999 | Hood |
| 6,005,767 A | 12/1999 | Ku |
| 6,008,809 A | 12/1999 | Brooks |
| 6,024,089 A | 2/2000 | Wallace |
| 6,042,548 A | 3/2000 | Giuffre |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,115,643 A | 9/2000 | Stine |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,167,401 A | 12/2000 | Csipkes |

(56) References Cited

U.S. PATENT DOCUMENTS

| | | |
|---|---|---|
| 6,188,407 B1 | 2/2001 | Smith |
| 6,221,012 B1 | 4/2001 | Maschke |
| 6,269,813 B1 | 8/2001 | Fitzgerald |
| 6,322,502 B1 | 11/2001 | Schoenberg |
| 6,338,823 B1 | 1/2002 | Furukawa |
| 6,339,732 B1 | 1/2002 | Phoon |
| 6,347,310 B1 | 2/2002 | Passera |
| 6,349,436 B1 | 2/2002 | Kreuzer |
| 6,364,834 B1 | 4/2002 | Reuss |
| 6,383,136 B1 | 5/2002 | Jordan |
| 6,396,583 B1 | 5/2002 | Clare |
| 6,406,426 B1 | 6/2002 | Reuss |
| 6,416,471 B1 | 7/2002 | Kumar |
| 6,424,860 B1 | 7/2002 | Karlsson |
| 6,435,690 B1 | 8/2002 | Till |
| 6,443,889 B1 | 9/2002 | Groth |
| D467,001 S | 12/2002 | Buczek |
| 6,488,029 B1 | 12/2002 | Hood |
| 6,536,430 B1 | 3/2003 | Smith |
| 6,541,758 B2 | 4/2003 | Yashiro |
| 6,554,238 B1 | 4/2003 | Hibberd |
| 6,571,227 B1 | 5/2003 | Agrafiotis |
| 6,571,792 B1 | 6/2003 | Hendrickson |
| 6,591,694 B2 | 7/2003 | Tsai |
| 6,600,662 B1 | 7/2003 | Emmert |
| 6,647,341 B1 | 11/2003 | Golub |
| 6,650,779 B2 | 11/2003 | Vachtesvanos |
| 6,674,837 B1 | 1/2004 | Taskar |
| 6,692,258 B1 | 2/2004 | Kurzweil |
| 6,692,436 B1 | 2/2004 | Bluth |
| 6,699,187 B2 | 3/2004 | Webb |
| 6,702,754 B2 | 3/2004 | Ogura |
| 6,715,722 B2 | 4/2004 | Roberts |
| 6,722,010 B2 | 4/2004 | Maruyama |
| 6,725,184 B1 | 4/2004 | Gadh |
| 6,735,648 B2 | 5/2004 | Onishi |
| 6,771,172 B1 | 8/2004 | Robinson |
| 6,790,178 B1 | 9/2004 | Mault |
| 6,796,264 B1 | 9/2004 | Appenzeller |
| 6,804,656 B1 | 10/2004 | Rosenfeld |
| 6,824,539 B2 | 11/2004 | Novak |
| 6,829,501 B2 | 12/2004 | Nielsen |
| 6,868,495 B1 | 3/2005 | Glover |
| 6,896,241 B2 | 5/2005 | Chen |
| 6,931,795 B1 | 8/2005 | Baloga |
| 6,933,931 B2 | 8/2005 | Lubarsky, Jr. |
| 6,944,561 B2 | 9/2005 | Tseng |
| 6,985,762 B2 | 1/2006 | Brashears |
| 7,006,865 B1 | 2/2006 | Cohen |
| 7,013,833 B2 | 3/2006 | Lemberger |
| 7,024,569 B1 | 4/2006 | Wright |
| 7,031,857 B2 | 4/2006 | Tarassenko |
| 7,038,588 B2 | 5/2006 | Boone |
| 7,040,175 B1 | 5/2006 | Huang |
| 7,055,232 B2 | 6/2006 | Maruyama |
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,128,709 B2 | 10/2006 | Saruya |
| 7,137,951 B2 | 11/2006 | Pilarski |
| 7,193,233 B2 | 3/2007 | Smith |
| 7,216,802 B1 | 5/2007 | De La Huerga |
| 7,219,559 B2 | 5/2007 | Sugi |
| 7,223,007 B1 | 5/2007 | Fredley |
| 7,234,944 B2 | 6/2007 | Nordin |
| 7,256,708 B2 | 8/2007 | Rosenfeld |
| 7,265,676 B2 | 9/2007 | Gordon |
| 7,267,666 B1 | 9/2007 | Duchon |
| 7,282,029 B1 | 10/2007 | Poulsen |
| 7,310,544 B2 | 12/2007 | Brister |
| 7,315,825 B1 | 1/2008 | Rosenfeld |
| 7,319,386 B2 | 1/2008 | Collins, Jr. |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,439,856 B2 | 10/2008 | Weiner |
| 7,468,032 B2 | 12/2008 | Stahmann |
| 7,469,601 B2 | 12/2008 | Sugi |
| 7,489,250 B2 | 2/2009 | Bock |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,530,949 B2 | 5/2009 | AlAli |
| 7,540,187 B1 | 6/2009 | Dillon |
| 7,556,039 B1 | 7/2009 | Peirry |
| 7,566,307 B2 | 7/2009 | Inukai |
| 7,621,500 B2 | 11/2009 | Ishizaki |
| 7,704,212 B2 | 4/2010 | Wekell |
| 7,710,567 B1 | 5/2010 | Mentzer |
| 7,751,878 B1 | 7/2010 | Merkle |
| 7,756,722 B2 | 7/2010 | Levine |
| 7,831,670 B2 | 11/2010 | Goodman |
| 7,836,882 B1 | 11/2010 | Rumph |
| 7,945,452 B2 | 5/2011 | Fathallah |
| 7,974,924 B2 | 7/2011 | Holla |
| 8,002,701 B2 | 8/2011 | John |
| 8,027,846 B2 | 9/2011 | Schoenberg |
| 8,033,686 B2 | 10/2011 | Recker |
| 8,091,422 B2 | 1/2012 | Felske |
| 8,147,419 B2 | 4/2012 | Krauss |
| 8,190,900 B2 | 5/2012 | Corndorf |
| 8,233,272 B2 | 7/2012 | Fidacaro |
| 8,273,018 B1 | 9/2012 | Fackler |
| 8,344,847 B2 | 1/2013 | Moberg |
| 8,398,408 B1 | 3/2013 | Hansen |
| 8,413,271 B2 | 4/2013 | Blanchard |
| 8,544,406 B2 | 10/2013 | Fujihira |
| 8,593,275 B2 | 11/2013 | Davis |
| 8,704,666 B2 | 4/2014 | Baker, Jr. |
| 8,798,527 B2 | 8/2014 | Gaines |
| 8,811,888 B2 | 8/2014 | Wiesner |
| 8,818,260 B2 | 8/2014 | Gaines |
| 8,855,550 B2 | 10/2014 | Gaines |
| 8,868,028 B1 | 10/2014 | Kaltsukis |
| 8,897,198 B2 | 11/2014 | Gaines |
| 8,903,308 B2 | 12/2014 | Wiesner |
| 8,922,330 B2 | 12/2014 | Moberg |
| 8,931,702 B2 | 1/2015 | Wekell |
| 8,940,147 B1 | 1/2015 | Bartsch |
| 8,943,168 B2 | 1/2015 | Wiesner |
| 9,020,419 B2 | 4/2015 | Gaines |
| 9,086,313 B2 | 7/2015 | Tobia |
| 9,844,637 B2 | 12/2017 | Beduhn |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0013517 A1 | 1/2002 | West |
| 2002/0026941 A1 | 3/2002 | Biondi |
| 2002/0032386 A1 | 3/2002 | Sackner |
| 2002/0040954 A1 | 4/2002 | Roberts |
| 2002/0060247 A1 | 5/2002 | Krishnaswamy |
| 2002/0095424 A1 | 7/2002 | Chung |
| 2002/0108011 A1 | 8/2002 | Tanha |
| 2002/0138017 A1 | 9/2002 | Bui |
| 2002/0161291 A1 | 10/2002 | Kianl |
| 2002/0173991 A1 | 11/2002 | Avitall |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0092974 A1 | 5/2003 | Santoso |
| 2003/0114836 A1 | 6/2003 | Estes |
| 2003/0117296 A1 | 6/2003 | Seely |
| 2003/0120164 A1 | 6/2003 | Nielsen |

(56) References Cited

U.S. PATENT DOCUMENTS

| | | |
|---|---|---|
| 2003/0130590 A1 | 7/2003 | Bui |
| 2003/0135087 A1 | 7/2003 | Hickle |
| 2003/0144699 A1 | 7/2003 | Freeman |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0008825 A1 | 1/2004 | Seeley |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0113895 A1 | 6/2004 | Lubarsky |
| 2004/0116813 A1 | 6/2004 | Selzer |
| 2004/0117209 A1 | 6/2004 | Brown |
| 2004/0117233 A1 | 6/2004 | Rapp |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | NecolaShehada |
| 2004/0240167 A1 | 12/2004 | Ledbetter |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0113704 A1 | 5/2005 | Lawson |
| 2005/0124866 A1 | 6/2005 | Elaz |
| 2005/0139213 A1 | 6/2005 | Blike |
| 2005/0146431 A1 | 7/2005 | Hastings |
| 2005/0148890 A1 | 7/2005 | Hastings |
| 2005/0151640 A1 | 7/2005 | Hastings |
| 2005/0177096 A1 | 8/2005 | Bollish |
| 2005/0192845 A1 | 9/2005 | Brinsfield |
| 2005/0193263 A1 | 9/2005 | Watt |
| 2005/0229110 A1 | 10/2005 | Gegner |
| 2005/0251232 A1 | 11/2005 | Hartley |
| 2006/0004475 A1 | 1/2006 | Brackett |
| 2006/0013462 A1 | 1/2006 | NavidSadikali |
| 2006/0022096 A1 | 2/2006 | Chan |
| 2006/0042635 A1 | 3/2006 | Niklewski |
| 2006/0053034 A1 | 3/2006 | Hlathein |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0161295 A1 | 7/2006 | Yun |
| 2006/0199618 A1 | 9/2006 | Steer |
| 2006/0213517 A1 | 9/2006 | Mashak |
| 2006/0226992 A1 | 10/2006 | Al-Ali |
| 2006/0258926 A1 | 11/2006 | Ali |
| 2006/0261781 A1 | 11/2006 | Oberding |
| 2006/0272141 A1 | 12/2006 | Rudduck |
| 2006/0278270 A1 | 12/2006 | Jones |
| 2006/0280621 A1 | 12/2006 | Kinugawa |
| 2006/0282302 A1 | 12/2006 | Hussain |
| 2006/0290525 A1 | 12/2006 | Andersen |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0047797 A1 | 3/2007 | Vilella |
| 2007/0050715 A1 | 3/2007 | Behar |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | DePaepe |
| 2007/0136023 A1 | 6/2007 | Schoenborn |
| 2007/0176931 A1 | 8/2007 | Tivig |
| 2007/0180140 A1 | 8/2007 | Welch |
| 2007/0199388 A1 | 8/2007 | Furkert |
| 2007/0199566 A1 | 8/2007 | Be |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0077435 A1 | 3/2008 | Muradia |
| 2008/0103375 A1 | 5/2008 | Kiani |
| 2008/0117029 A1 | 5/2008 | Dohrmann |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0194918 A1 | 8/2008 | Kulik |
| 2008/0208381 A1 | 8/2008 | Soga |
| 2008/0221418 A1 | 9/2008 | Al-Ali |
| 2008/0221495 A1 | 9/2008 | Steffens |
| 2008/0228045 A1 | 9/2008 | Gao |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005651 A1 | 1/2009 | Ward |
| 2009/0005703 A1 | 1/2009 | Fasciano |
| 2009/0015116 A1 | 1/2009 | Arceta |
| 2009/0024008 A1 | 1/2009 | Brunner |
| 2009/0043171 A1 | 2/2009 | Rule |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0076397 A1 | 3/2009 | Libbus |
| 2009/0099480 A1 | 4/2009 | Salgo |
| 2009/0117784 A1 | 5/2009 | Wu |
| 2009/0121592 A1 | 5/2009 | De Nando |
| 2009/0124239 A1 | 5/2009 | Tsuei |
| 2009/0131805 A1 | 5/2009 | OBrien |
| 2009/0133609 A1 | 5/2009 | Nethken |
| 2009/0149901 A1 | 6/2009 | Jayne |
| 2009/0151720 A1 | 6/2009 | Inoue |
| 2009/0182204 A1 | 7/2009 | Semler |
| 2009/0190713 A1 | 7/2009 | Wai |
| 2009/0192541 A1 | 7/2009 | Ortiz |
| 2009/0193315 A1 | 7/2009 | Gower |

(56) References Cited

U.S. PATENT DOCUMENTS

| | | |
|---|---|---|
| 2009/0200902 A1 | 8/2009 | McKay |
| 2009/0206713 A1 | 8/2009 | Vilkas |
| 2009/0209849 A1 | 8/2009 | Rowe |
| 2009/0213034 A1 | 8/2009 | Wu |
| 2009/0237264 A1 | 9/2009 | Bobey |
| 2009/0248173 A1 | 10/2009 | Sasko |
| 2009/0275805 A1 | 11/2009 | Lane |
| 2009/0326340 A1 | 12/2009 | Wang |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0056877 A1 | 3/2010 | Fein |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1* | 6/2010 | Pierry .................. A61B 5/083 600/529 |
| 2010/0156655 A1 | 6/2010 | Bullemer |
| 2010/0164452 A1 | 7/2010 | Ruan |
| 2010/0175695 A1 | 7/2010 | Jamison |
| 2010/0179400 A1 | 7/2010 | Brauker |
| 2010/0198027 A1 | 8/2010 | Dixon |
| 2010/0233891 A1 | 9/2010 | Broeksteeg |
| 2010/0238138 A1 | 9/2010 | Goertz |
| 2010/0259881 A1 | 10/2010 | Choi |
| 2010/0261979 A1 | 10/2010 | Kiani |
| 2010/0273530 A1 | 10/2010 | Jarvis |
| 2010/0282256 A1 | 11/2010 | Loescher |
| 2010/0285771 A1 | 11/2010 | Peabody |
| 2010/0294405 A1 | 11/2010 | Longinotti-Buitoni |
| 2010/0298655 A1 | 11/2010 | McCombie |
| 2010/0298656 A1 | 11/2010 | McCombie |
| 2010/0298718 A1 | 11/2010 | Gilham |
| 2010/0318578 A1 | 12/2010 | Treu |
| 2010/0324380 A1 | 12/2010 | Perkins |
| 2010/0324384 A1 | 12/2010 | Moon |
| 2010/0324936 A1 | 12/2010 | Vishnubhatla |
| 2011/0004071 A1 | 1/2011 | Faiola |
| 2011/0006876 A1 | 1/2011 | Moberg |
| 2011/0015493 A1 | 1/2011 | Koschek |
| 2011/0054267 A1 | 3/2011 | Fidacaro |
| 2011/0055205 A1 | 3/2011 | Scott |
| 2011/0071420 A1 | 3/2011 | Pierre |
| 2011/0077971 A1 | 3/2011 | Surwit |
| 2011/0087756 A1 | 4/2011 | Biondi |
| 2011/0088694 A1 | 4/2011 | Tobia |
| 2011/0092838 A1 | 4/2011 | Helfenbein |
| 2011/0125040 A1 | 5/2011 | Crawford |
| 2011/0130798 A1 | 6/2011 | Elghazzawi |
| 2011/0138323 A1 | 6/2011 | Skidmore |
| 2011/0146676 A1 | 6/2011 | Dallam |
| 2011/0152629 A1 | 6/2011 | Eaton |
| 2011/0164074 A1 | 7/2011 | Frank |
| 2011/0190643 A1 | 8/2011 | Zhang |
| 2011/0224531 A1 | 9/2011 | Steiner |
| 2011/0225771 A1 | 9/2011 | Bartnick |
| 2011/0227739 A1 | 9/2011 | Gilham |
| 2011/0245579 A1 | 10/2011 | Bruggeman |
| 2011/0257489 A1 | 10/2011 | Banet |
| 2011/0270058 A1 | 11/2011 | Price |
| 2011/0279383 A1 | 11/2011 | Wilson |
| 2011/0279958 A1 | 11/2011 | Clark |
| 2011/0295426 A1 | 12/2011 | Georgeson |
| 2011/0298718 A1 | 12/2011 | Chang |
| 2012/0030610 A1 | 2/2012 | DiPerna |
| 2012/0041783 A1 | 2/2012 | McKee |
| 2012/0041786 A1 | 2/2012 | Yu |
| 2012/0075060 A1 | 3/2012 | Connor |
| 2012/0075327 A1 | 3/2012 | Mackenzie |
| 2012/0083906 A1 | 4/2012 | Weatherhead |
| 2012/0093311 A1 | 4/2012 | Nierzwick |
| 2012/0095778 A1 | 4/2012 | Gross |
| 2012/0101396 A1 | 4/2012 | Solosko |
| 2012/0105233 A1 | 5/2012 | Bobey |
| 2012/0105774 A1 | 5/2012 | Fletcher |
| 2012/0108991 A1 | 5/2012 | Song |
| 2012/0116331 A1 | 5/2012 | Locke |
| 2012/0127103 A1 | 5/2012 | Qualey |
| 2012/0136231 A1 | 5/2012 | Markel |
| 2012/0180789 A1 | 7/2012 | Tobia |
| 2012/0184120 A1 | 7/2012 | Basta |
| 2012/0186583 A1 | 7/2012 | Drapes |
| 2012/0203491 A1 | 8/2012 | Sun |
| 2012/0209984 A1 | 8/2012 | Gonzalez-Banos |
| 2012/0232398 A1 | 9/2012 | Roham |
| 2012/0233679 A1 | 9/2012 | Shedrinsky |
| 2012/0245439 A1 | 9/2012 | Andre |
| 2012/0265089 A1 | 10/2012 | Orr |
| 2012/0330675 A1 | 12/2012 | Muradia |
| 2013/0015966 A1 | 1/2013 | Soomro |
| 2013/0030258 A1 | 1/2013 | Cheung |
| 2013/0107445 A1 | 5/2013 | Reber |
| 2013/0162426 A1 | 6/2013 | Wiesner |
| 2013/0267861 A1 | 10/2013 | Vassallo |
| 2014/0142963 A1 | 5/2014 | Hill |
| 2014/0153747 A1 | 6/2014 | Contolini |
| 2014/0275873 A1 | 9/2014 | Fries |
| 2014/0337777 A1 | 11/2014 | Senesac |
| 2015/0018703 A1 | 1/2015 | Shetty |

FOREIGN PATENT DOCUMENTS

| | | |
|---|---|---|
| CN | 1518427 A | 8/2004 |
| CN | 1593764 A | 3/2005 |
| CN | 1688256 | 10/2005 |
| CN | 1781107 A | 5/2006 |
| CN | 1839311 A | 9/2006 |
| CN | 1943505 A | 4/2007 |
| CN | 1983258 A | 6/2007 |
| CN | 100391403 C | 6/2008 |
| CN | 101194278 | 6/2008 |
| CN | 101496923 | 8/2009 |
| CN | 101501683 | 8/2009 |
| CN | 101521845 | 9/2009 |
| CN | 101547716 A | 9/2009 |
| CN | 101611410 | 12/2009 |
| CN | 201570216 U | 9/2010 |
| CN | 201594642 U | 9/2010 |
| CN | 101893916 | 11/2010 |
| CN | 201708829 U | 1/2011 |
| CN | 102184312 | 9/2011 |
| CN | 102567624 | 7/2012 |
| DE | 9415672 | 11/1994 |
| DE | 102006011151 | 9/2007 |
| EP | 0596509 | 5/1994 |
| EP | 0686900 | 12/1995 |
| EP | 0686900 A2 | 12/1995 |
| EP | 0955007 A1 | 11/1999 |
| EP | 1054338 | 11/2000 |
| EP | 1227752 A1 | 5/2001 |
| EP | 1449558 | 8/2004 |
| EP | 1852060 | 11/2007 |
| EP | 1868123 A1 | 12/2007 |
| EP | 1197178 | 7/2008 |
| EP | 2555668 A2 | 2/2013 |
| EP | 2641151 | 9/2013 |
| EP | 2651482 | 10/2013 |
| EP | 2709518 | 3/2014 |
| EP | 2805564 A4 | 9/2015 |
| GB | 191214095 | 10/1912 |
| GB | 568212 | 3/1945 |
| GB | 2348715 | 10/2000 |
| GB | 2389290 A | 12/2003 |
| GB | 2438495 | 11/2007 |
| JP | 13286735 | 12/1991 |
| JP | 05143611 | 6/1993 |
| JP | 15184550 | 7/1993 |
| JP | 15341771 | 12/1993 |
| JP | 07163527 | 6/1995 |
| JP | 08504345 | 5/1996 |
| JP | 08504531 | 5/1996 |
| JP | 08275926 | 10/1996 |

(56) References Cited

FOREIGN PATENT DOCUMENTS

| | | |
|---|---|---|
| JP | 19108194 | 4/1997 |
| JP | 3059292 | 7/1999 |
| JP | 2001052281 | 2/2001 |
| JP | 2003210422 | 7/2003 |
| JP | 2004208855 | 7/2004 |
| JP | 2005529396 | 9/2005 |
| JP | 2008520026 | 6/2008 |
| JP | 2008532587 | 8/2008 |
| JP | 2009054381 | 3/2009 |
| JP | 2009211589 | 9/2009 |
| JP | 2009245435 | 10/2009 |
| JP | 2009544431 | 12/2009 |
| JP | 2010086535 | 4/2010 |
| JP | 2011078640 | 4/2011 |
| JP | 2012529926 | 11/2012 |
| WO | 9415523 A1 | 7/1994 |
| WO | 1994015523 | 7/1994 |
| WO | 1999018705 | 4/1999 |
| WO | 1999027326 | 6/1999 |
| WO | 2000042911 | 7/2000 |
| WO | 0134023 | 5/2001 |
| WO | 03091841 | 11/2003 |
| WO | 03102850 | 12/2003 |
| WO | 2004038669 A1 | 5/2004 |
| WO | 2004070994 A2 | 8/2004 |
| WO | 2005101276 A3 | 10/2005 |
| WO | 2005114524 A3 | 12/2005 |
| WO | 2006090371 | 8/2006 |
| WO | 2006094055 A2 | 9/2006 |
| WO | 2008005921 A1 | 1/2008 |
| WO | 2010126797 | 11/2010 |
| WO | 2010126916 | 11/2010 |
| WO | 2010126916 A1 | 11/2010 |
| WO | 2011001302 | 1/2011 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |
| WO | 2014055660 A1 | 4/2014 |
| WO | 2014194193 | 12/2014 |

OTHER PUBLICATIONS

*Aerotel Ltd* v *Telco Holdings Ltd* Ord Rev 1 [2007] RPC 7 (Aerotel/Macrossam).
*Symbian* v *Comptroller General of Patents* [2008] EWCA Civ 1066.
*AT&T Knowledge Ventures LP and Cvon Innovations Ltd* v *Comptroller General of patents* [2009] EWHX 343 (Pat).
*HTC Europe Co Ltd* v *Apple linc* [2013] EWCA Civ 451.
*Lantana* v *Comptroller-General of Patents* [2013] EWHC 2673 (Pat).
Chinese Office Action, Patent Application No. 201180025170X, dated Apr. 21, 2014, First OA.
European Search Report for EP12786443.7, dated Apr. 15, 2015.
IntelliVue Patient Monitor; MP20/30, MP40/50, MP60/70/80/90, Release G.0 with Software Revision G.0x.xx (Philips) Sep. 2008; pp. 4, 10, 19, 20, 46-49, 82, 326, 348, 420, 422, 424, 452; Accessed on Sep. 30, 2013: <http://www.mc.vanderbilt.edu/documents/nursingeducationresources/files/MP20-MP90%20Instructions%20for%20Use%20Manual%20Rev_G_0%20%20English%20M8000-9001K.pdf>.
International Preliminary Report on Patentability, PCT/US12/38000, dated Nov. 13, 2013.
International Preliminary Report on Patentability, PCT/US2006/007269, dated Sep. 11, 2007, Spacelabs Medical.
International Preliminary Report on Patentability, PCT/US2011/028007, dated Sep. 17, 2013, International Search Authority.
International Preliminary Report on Patentability, PCT/US2011/065678, dated Jun. 18, 2013, International Search Authority.
International Preliminary Report on Patentability, PCT/US2011/065685, dated Jun. 18, 2013.
International Preliminary Report on Patentability for PCT/US2011/061554, dated Feb. 25, 2014.
International Search Report, PCT/US2011/028007, dated Jul. 11, 2011, International Search Authority.
International Search Report, PCT/US2011/065685, dated May 8, 2012, International Search Authority.
International Search Report for PCT/US06/07269, dated Aug. 28, 2006.
International Search Report for PCT/US10/32635, dated Jul. 23, 2010.
International Search Report for PCT/US10/34025, dated Aug. 9, 2010.
International Search Report for PCT/US12/38000, dated Oct. 23, 2012.
International Search Report for PCT/US2010/052977, dated Mar. 18, 2011.
International Search Report for PCT/US2011/029278, dated Aug. 2, 2011.
International Search Report for PCT/US2011/061554, dated Feb. 14, 2014.
International Search Report for PCT/US2011/061555, dated Apr. 17, 2012.
International Search Report for PCT/US2011/061558, dated Aug. 10, 2012.
International Search Report for PCT/US2011/065676, dated Sep. 20, 2012.
International Search Report for PCT/US2011/065678, dated Jun. 29, 2012.
International Search Report for PCT/US2011/61557, dated Apr. 23, 2012.
International Search Report for PCT/US2012/060125, dated Apr. 19, 2013.
International Search Report for PCT/US2013/041246, dated Dec. 9, 2013.
International Search Report for PCT/US2013/041247, dated Jan. 10, 2014.
International Search Report for PCT/US2013/063087, dated Mar. 6, 2014.
International Search Report for PCT/US2014/040225, dated Nov. 5, 2014.
Notice of Allowance dated Jan. 28, 2015 for U.S. Appl. No. 13/300,478.
Notice of Allowance dated Jan. 8, 2015 for U.S. Appl. No. 13/329,259.
Notice of Allowance dated Mar. 13, 2015 for U.S. Appl. No. 12/906,081.
Notice of Allowance dated May 11, 2015 for U.S. Appl. No. 13/300,462.
Notice of Allowance dated May 27, 2015 for U.S. Appl. No. 14/165,193.
Notice of Allowance dated Oct. 31, 2014 for U.S. Appl. No. 12/114,689.
Office Action dated Apr. 24, 2015 for U.S. Appl. No. 13/651,337.
Office Action dated Apr. 7, 2015 for U.S. Appl. No. 13/472,332.
Office Action dated Aug. 14, 2014 for U.S. Appl. No. 12/768,714.
Office Action dated Dec. 10, 2014 for U.S. Appl. No. 14/165,193.
Office Action dated Feb. 26, 2015 for U.S. Appl. No. 12/768,714.
Office Action dated Jan. 17, 2013 for U.S. Appl. No. 12/768,714.
Office Action dated Jul. 2, 2015 for U.S. Appl. No. 13/895,527.
Office Action dated Jun. 18, 2012 for U.S. Appl. No. 12/768,714.
Office Action dated Jun. 18, 2015 for U.S. Appl. No. 13/329,186.
Office Action dated May 21, 2015 for U.S. Appl. No. 13/300,526.
Office Action dated May 31, 2013 for U.S. Appl. No. 13/052,883.
Office Action dated May 9, 2016 for U.S. Appl. No. 13/472,332.

(56) References Cited

OTHER PUBLICATIONS

Office Action dated Nov. 12, 2014 for U.S. Appl. No. 13/300,462.
Office Action dated Nov. 13, 2015 for U.S. Appl. No. 13/472,332.
Office Action dated Nov. 21, 2013 for U.S. Appl. No. 12/768,714.
Office Action dated Nov. 21, 2014 for U.S. Appl. No. 13/045,539.
Office Action dated Sep. 22, 2014 for U.S. Appl. No. 13/329,186.
Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
Supplemental Notice of Allowance dated Apr. 20, 2015 for U.S. Appl. No. 12/906,081.
Supplementary European Search Report, dated Nov. 25, 2009, Spacelabs Medical, PCT/US2006/007269.
"BleaseSirius Anesthesia Systems User Manual 1073-0212-00/ REV. B", Dec. 1, 2010, pp. 1-258, XP055209666.
"Lifegard II Patient Monitor Operator's Manual", Jan. 1, 2006, pp. 1-1, XP055209485.
Extended European Search Report, EP 11861868.5, dated Sep. 28, 2015.
Extended European Search Report for EP12839321, dated Dec. 1, 2015.
First Office Action, Chinese Patent Application No. 201180067543. X, dated Jun. 2014.
First Office Action, Chinese Patent Application No. 2012800351488, dated Jun. 13, 2015.
Google patents search, Sep. 25, 2015, U.S. Appl. No. 14/044,524.
Notice of Allowance dated Nov. 18, 2015 for U.S. Appl. No. 14/557,135.
Notice of Allowance dated Sep. 3, 2014 for U.S. Appl. No. 13/973,862.
Office Action dated Apr. 16, 2015 for U.S. Appl. No. 14/557,135.
Office Action dated Aug. 1, 2011 for U.S. Appl. No. 11/716,513.
Office Action dated Aug. 28, 2009 for U.S. Appl. No. 11/716,513.
Office Action dated Aug. 4, 2015 for U.S. Appl. No. 13/329,219.
Office Action dated Aug. 6, 2015 for U.S. Appl. No. 13/045,539.
Office Action dated Feb. 10, 2016 for U.S. Appl. No. 13/895,270.
Office Action dated Feb. 11, 2016 for U.S. Appl. No. 13/895,281.
Office Action dated Feb. 9, 2016 for U.S. Appl. No. 13/045,539.
Office Action dated Jan. 15, 2016 for U.S. Appl. No. 14/312,566.
Office Action dated Jan. 20, 2016 for U.S. Appl. No. 13/651,337.
Office Action dated Jul. 2, 2012 for U.S. Appl. No. 11/716,513.
Office Action dated Mar. 23, 2010 for U.S. Appl. No. 11/716,513.
Office Action dated Oct. 14, 2015 for U.S. Appl. No. 14/460,147.
Office Action dated Oct. 2, 2015 for U.S. Appl. No. 14/044,524.
Office Action dated Oct. 7, 2015 for U.S. Appl. No. 12/768,714.
Office Action for Chinese Patent Application No. 201080057413.3, dated Oct. 10, 2015.
Office Action for Chinese Patent Application No. 2011800655173, dated May 15, 2015.
Office Action for Chinese Patent Application No. 2011800707731, dated Sep. 29, 2015.
Office Action dated Jan. 6, 2016 for U.S. Appl. No. 13/329,219.
Partial European Search Report for EP 12839321.2, dated May 26, 2015.
Second Office Action, Chinese Patent Application No. 201180025170X, dated Jun. 7, 2015.
Second Office Action for Chinese Patent Application No. 201180067543. X, dated Nov. 11, 2015.
Third Office Action, Chinese Patent Application No. 201180025170X, dated Dec. 10, 2015.
Examination Report for GB12169124, dated Dec. 2, 2015.
First Office Action for Chinese Patent Application No. CN2011800653708, dated Feb. 3, 2016.
Notice of Allowance dated Mar. 2, 2016 for U.S. Appl. No. 14/460,147.
Notice of Allowance dated May 20, 2016 for U.S. Appl. No. 14/312,566.
Office Action dated Apr. 1, 2016 for U.S. Appl. No. 13/329,186.
Office Action for Mexican Patent Application No. 2014013947, dated Feb. 26, 2016.
Supplementary European Search Report for EP13790605, completed on Feb. 29, 2016.
Office Action dated Jul. 12, 2016 for U.S. Appl. No. 14/044,524.
Second Office Action, Chinese Patent Application No. 2012800351488, dated Dec. 10, 2015.
First Office Action for CN2011800655972, dated Nov. 5, 2015.
Office Action dated Jul. 14, 2016 for U.S. Appl. No. 13/329,186.
Second Office Action for Mexican Patent Application No. 2014013947, dated Jul. 28, 2016.
Supplementary Partial European Search Report for EP13790154, completed on Feb. 11, 2016.
Philips: 'IntelliVue Patient Monitor; MP20/30, MP40/50, MP60/ 70/80/90', Internet Citation, Sep. 1, 2008, pp. 2PP, I-X, 1, XP003034216.
Anonymous: 'Docking station-wikipedia, the free encyclopedia', Feb. 20, 2012, XP055284610.
Anonymous: 'Pogo pin-wikipedia, the free encyclopedia', Apr. 28, 2012, XP055284974.
Supplementary European Search Report for EP13790154, completed on Jul. 1, 2016.
First Office Action for CN201380037855.5, dated Dec. 21, 2015.
Office Action for CN201380060910.2, dated Jul. 13, 2016.
Examination Report for GB1321385.5, dated Mar. 31, 2016.
Office Action dated Sep. 15, 2016 for U.S. Appl. No. 13/895,270.
Office Action dated Nov. 9, 2016 for U.S. Appl. No. 13/472,332.
Notice of Allowance dated Nov. 7, 2016 for U.S. Appl. No. 13/651,337.
Examination Report for GB12169124, dated Apr. 21, 2016.
Examination Report for GB12169124, dated Feb. 15, 2016.
Examination Report for GB13108402, dated Sep. 30, 2016.
Examination Report for GB13108402, dated Nov. 3, 2016.
Second Office Action for CN2011800655972, dated May 24, 2016.
Office Action dated Dec. 9, 2016 for U.S. Appl. No. 12/768,714.
Notice of Allowance dated Dec. 22, 2016 for U.S. Appl. No. 13/045,539.
Anonymous: "Routing table", Wikipedia, Oct. 3, 2012 (Oct. 3, 2012), XP055321398, Retrieved from the Internet: URL: https:// en.wikipedia.org/w/index.php?title=Routing_table&oldid= 515747820, [retrieved on Nov. 21, 2016].
Anonymous: "Metrics (networking)", Wikipedia, Jul. 18, 2012 (Jul. 18, 2012), XP055321558, Retrieved from the Internet: URL: https:// en.wikipedia.org/w/index.php?title=Metrics_(networking)&oldid= 502970743, [retrieved on Nov. 22, 2016].
Supplementary European Search Report for EP13843278, completed on Nov. 22, 2016.
Office Action dated Jan. 25, 2017 for U.S. Appl. No. 13/895,270.
Office Action dated Mar. 9, 2017 for U.S. Appl. No. 13/895,281.
Examination Report for GB1321385.5, dated Aug. 22, 2016.
Examination Report for GB1321385.5, dated Jan. 25, 2017.
Supplementary European Search Report for EP11842166, completed on Jan. 18, 2017.
Fourth Office Action, Chinese Patent Application No. 201180025170X, dated Jun. 20, 2016.
GE Healthcare, Modular monitoring for critical care, iMM Solar 8000i and iMM Transport Pro Monitors, 2005.
GE Healthcare, CARESCAPE Monitor B850, Engineered to help provide better care, 2009.
Office Action dated Jun. 23, 2017 for U.S. Appl. No. 13/300,526; (pp. 1-13).
Office Action dated Jun. 29, 2017 for U.S. Appl. No. 13/472,332; (pp. 1-23).
Office Action for Japanese Patent Application No. JP2014511465, dated Dec. 14, 2015.
Office Action for Japanese Patent Application No. JP2014511465, dated Nov. 4, 2016.
Examination Report for Australian Patent Application No. 2012255897, dated Nov. 4, 2015.
Office Action dated Aug. 23, 2017 for U.S. Appl. No. 13/895,270; (pp. 1-10).
Exam Report for GB1310778.4, dated Dec. 1, 2016.
Exam Report for GB1310778.4, dated Feb. 24, 2017.

(56) References Cited

OTHER PUBLICATIONS

Rejection Decision, Chinese Patent Application No. 2012800351488, dated Apr. 28, 2017.
Third Office Action, Chinese Patent Application No. 2012800351488, dated Nov. 18, 2016.
Supplementary European Search Report for EP10823756, completed on Oct. 4, 2017.
Supplementary European Search Report for EP10824231, completed on Oct. 16, 2017.
Examination Report for GB1311848.4, dated Oct. 18, 2016.
Second Office Action for Chinese Patent Application No. CN2011800653708, dated Dec. 12, 2016.
Third Office Action for CN2011800655972, dated Jan. 2017.
Second Office Action for CN201380037855.5, dated Aug. 24, 2016.
Third Office Action for CN201380037855.5, dated May 12, 2017.
Anonymous: "Framebuffer—Wkipedia, the free encyclopedia", Mar. 14, 2010, XP055307861, Retrieved from the Internet: URL—https://en.wikipedia.org/w/index.php?title=Framebuffer&oldid=349748376 [retrieved on Oct. 5, 2016].
Supplementary European Search Report for EP11760006, completed on Oct. 5, 2016.
Examination Report for Australian Application No. 2013327128, dated Jan. 13, 2016.
Office Action for CA2887029, dated Apr. 8, 2017.
Office Action for CA2887029, dated May 2, 2016.
Search and Examination Report for GB1711443.0, dated Oct. 11, 2017.
Examination Report for GB1407581.6, dated May 17, 2017.
Patent Examination Report No. 1 for AU2013262812, dated Feb. 3, 2016.
"IntelliVue Patient Monitor MP20/30, MP40/50, MP60/70/80/90 Release G.0 with Software Revision G.0X.XX" Sep. 2008; See particularly pp. 3-19.
Examination Report for GB1421959.6, dated Jun. 16, 2017.
Office Action for JP2015512811, dated Apr. 3, 2017.
First Office Action for CN2013800376013, dated Nov. 15, 2016.
Office Action for JP2015512812, dated Feb. 20, 2017.
Office Action dated Dec. 22, 2017 for U.S. Appl. No. 13/895,281; (pp. 1-13).
Office Action for CN201380060910.2, dated Jul. 2017.
Office Action for Japanese Patent Application No. JP2015535761, dated Oct. 30, 2017.
Examination Report for EP10770217.7, dated Nov. 17, 2017.
Office Action for CA2835937, dated Dec. 11, 2017.
Examination Report for GB1711443.0, dated Nov. 28, 2017.
Third Office Action for Chinese Patent Application No. CN2011800653708, dated Dec. 1, 2017.
First Office Action for CN2014800427908, dated Dec. 4, 2017.
Rejection Decision for CN201380037855.5, dated Nov. 6, 2107.
Examination Report for GB1421959.6, dated Feb. 16, 2018.
Further Search Report for GB1421959.6, dated Feb. 15, 2018.
Second Office Action for CN2013800376013, dated Sep. 19, 2017.
Office Action for MX/A/2014/013940, dated Oct. 2017.

\* cited by examiner

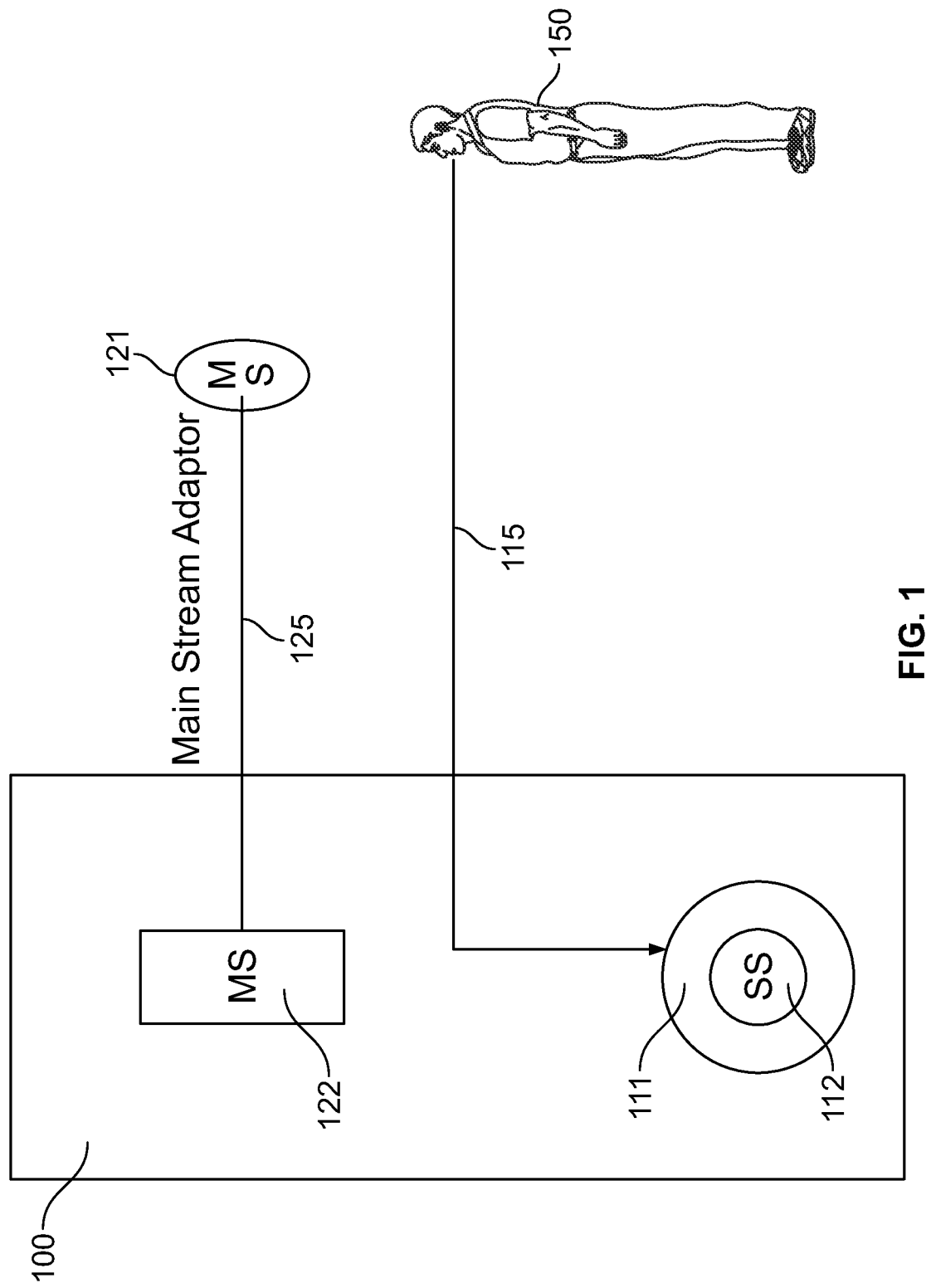

CAPNOGRAPHY MODULE WITH AUTOMATIC SWITCHING BETWEEN MAINSTREAM AND SIDESTREAM MONITORING

CROSS-REFERENCE

The present specification relies on U.S. Provisional Patent Application No. 61/829,222, entitled "Capnography Module with Automatic Switching Between Mainstream and Sidestream Monitoring" and filed on May 30, 2013, for priority, which is herein incorporated by reference in its entirety.

FIELD

The present specification relates generally to patient monitoring systems. More particularly, the present specification relates to a capnography module for a patient monitoring system that is capable of switching automatically between mainstream monitoring and sidestream monitoring.

BACKGROUND

A patient monitoring system is an electronic medical system that measures a patient's various vital signs, collects and processes all measurements as data, and then displays the data graphically and/or numerically on a viewing screen. Graphical data is displayed continuously as data channels on a time axis (waveforms). Patient monitoring systems are positioned near hospital beds, typically in critical care units, where they continually monitor patient status via measuring devices attached to the patient and can be viewed by hospital personnel. Some patient monitoring systems can only be viewed on a local display, whereas others can be joined to a network and thereby display data at other locations, such as central monitoring or nurses' stations.

Portable patient monitoring systems are available for use by emergency medical services (EMS) personnel. These systems typically include a defibrillator along with the monitor. Other portable units, such as Holter monitors, are worn by patients for a particular time period and then returned to the physician for evaluation of the measured and collected data. Current patient monitoring systems are able to measure and display a variety of vital signs, including, pulse oximetry ($SpO_2$), electrocardiograph (ECG), invasive blood pressure (IBP), non-invasive blood pressure (NIBP), electroencephalograph (EEG), body temperature, cardiac output, capnography ($CO_2$), mixed venous oxygen saturation ($SvO_2$), bispectral index (BISx), and respiration. Patient monitoring systems are capable of measuring and displaying maximum, minimum, and average values and frequencies, such as pulse and respiratory rates. Data collected can be transmitted through fixed wire connections or wireless data communication. Power to patient monitoring systems can be supplied through a main power line or by batteries.

Current patient monitoring systems typically include a capnography module. Capnography is the monitoring of the concentration or partial pressure of carbon dioxide ($CO_2$) in a patient's respiratory gases. Capnography is used typically during anesthesia and in intensive care units. $CO_2$ levels determined via capnography are used to monitor a patient's physiologic status and to assess the adequacy of ventilation during anesthesia. Capnography typically measures end tidal carbon dioxide ($ETCO_2$), which is the concentration or partial pressure of carbon dioxide at the end of a patient's exhalation, minimum carbon dioxide ($MinCO_2$), and respiratory rate. Capnography includes mainstream capnography and sidestream capnography. Mainstream capnography measures $CO_2$ levels via an in-line infrared sensor connected directly to the airway between an endotracheal tube and a breathing circuit. Sidestream capnography involves the collection of airway gas samples from the breathing circuit. $CO_2$ levels are then measured by an infrared sensor located in a remote monitoring unit.

While current capnography modules are effective in monitoring the $CO_2$ levels in patient respiratory gases, they are not without their drawbacks. For example, current capnography modules capable of both mainstream and sidestream monitoring require manual switching between the two analyzers. Manual switching between mainstream and sidestream monitoring often includes temporarily removing power from the module and/or rebooting the host interface capnography module. This can be time consuming and can result in a short period during which $CO_2$ levels are not monitored. Therefore, a need exists for a capnography module capable of both mainstream and sidestream monitoring wherein switching between the two analyzers is accomplished automatically without loss of power or module rebooting.

SUMMARY

The present specification discloses a capnography module for use with a patient monitoring system, said capnography module comprising: a monitor connector for connecting said capnography module to a monitor of said patient monitoring system, said monitor connector providing a pathway for data transmission between said capnography module and said patient monitoring system; a mainstream connector for connecting a mainstream capnography sensor to said capnography module; a sidestream port for connecting a sidestream sampling line to said capnography module; a mainstream gas values parser for analyzing data provided by a mainstream capnography sensor attached to said mainstream connector; a sidestream capnography sensor for monitoring gases provided by a sidestream sampling line attached to said sidestream port; a sidestream gas values parser for analyzing data provided by said sidestream capnography sensor; a hardware switching mechanism, comprising a plurality of circuits and communication interfaces between said circuits; a controller circuit in communication with said hardware switching mechanism and said monitor of said patient monitoring system; and, a software switching mechanism, comprising programmatic instructions stored on non-volatile memory, said software switching mechanism responsive to flags generated by said hardware switching mechanism and in communication with said controller circuit; wherein, when either one of said mainstream capnography sensor or said sidestream sampling line is physically attached to said mainstream connector or said sidestream port respectively, said hardware switching mechanism generates a flag indicative of the attached mainstream capnography sensor or sidestream sampling line, further wherein said software switching mechanism responds to said flag by notifying said controller circuit of the availability of either one of said mainstream gas values parser unit or said sidestream gas values parser unit, yet further wherein said controller circuit automatically operates said capnography module in a mainstream monitoring mode or a sidestream monitoring mode dependent upon which of said values parser units is available as indicated by said software switching mechanism.

Optionally, the capnography module further comprises a gas scavenging port.

Optionally, the capnography module further comprises a connector latching mechanism for securely attaching said mainstream capnography sensor to said mainstream connector to prevent accidental disconnection of said mainstream capnography sensor from said capnography module.

The hardware switching mechanism may comprise a power supply galvanic isolation circuit to protect said mainstream gas values parser unit from electrostatic discharge. Optionally, the hardware switching mechanism may further comprise a switch mode buck regulator for regulating DC power from said power supply galvanic isolation circuit and providing regulated 5 V power to said mainstream gas values parser unit.

Optionally, the hardware switching mechanism comprises a data and control lines galvanic isolation circuit to protect said mainstream gas values parser unit from electrostatic discharge.

Optionally, the hardware switching mechanism comprises a mainstream cold connected sensing circuit to detect the connection of a mainstream capnography sensor to said capnography module while said capnography module is operating in said sidestream operating mode and to maintain said capnography module in said sidestream operating mode. Optionally, the hardware switching mechanism further comprises a current sensing circuit, an amplifier and averaging circuit, and a comparator with open drain output for said mainstream gas values parser unit and a current sensing circuit, an amplifier and averaging circuit, and a comparator with open drain output for said sidestream gas values parser unit, wherein said circuits monitor the increase in current levels for said mainstream and sidestream gas values parser units respectively, when said mainstream capnography sensor and said sidestream sampling line are connected to said capnography module, further wherein said respective comparators notify said controller board of the availability of said respective gas values parser units when said current levels are high. Optionally, the hardware switching mechanism further comprises an OR gate for receiving signals from said mainstream cold connected sensing circuit and said comparator with open drain output for said mainstream gas values parser unit, further wherein said OR gate determines if said mainstream gas values parser unit is available based upon said signals.

Optionally, the mainstream gas values parser unit and the sidestream gas values parser unit are equipped with RS-232 voltage levels for data reception and transmission and said controller circuit operates at 5 V standard DC power, wherein said hardware switching mechanism comprises at least two RS-232 level translators for translating the RS-232 voltage levels of said gas values parser units to standard transistor-transistor logic (TTL) signal levels.

Optionally, the hardware switching mechanism comprises a double pole double through switch for controlling said software switching mechanism.

Optionally, the hardware switching mechanism comprises a select line comprising an I/O pin for toggling data input and output along with power switching between said mainstream gas values parser unit and said sidestream gas values parser unit.

Optionally, the mainstream connector comprises a 9 pin DE-9 mainstream values parser connector and the monitor connector comprises a synchronous data link control (SDLC) protocol with module power supply 15 pin male connector.

The present specification also discloses a method of switching automatically between mainstream monitoring and sidestream monitoring on a capnography module of a patient monitoring system, said method comprising the steps of: providing a capnography module for use with a patient monitoring system, said capnography module comprising: a monitor connector for connecting said capnography module to a monitor of said patient monitoring system, said monitor connector providing a pathway for data transmission between said capnography module and said patient monitoring system; a mainstream connector for connecting a mainstream capnography sensor to said capnography module; a sidestream port for connecting a sidestream sampling line to said capnography module; a mainstream gas values parser for analyzing data provided by a mainstream capnography sensor attached to said mainstream connector; a sidestream capnography sensor for monitoring gases provided by a sidestream sampling line attached to said sidestream port; a sidestream gas parser for analyzing data provided by said sidestream capnography sensor; a hardware switching mechanism, comprising a plurality of circuits and communication interfaces between said circuits; a controller circuit in communication with said hardware switching mechanism and said monitor of said patient monitoring system; and, a software switching mechanism, comprising programmatic instructions stored on non-volatile memory, said software switching mechanism responsive to flags generated by said hardware switching mechanism and in communication with said controller circuit; wherein, when either one of said mainstream capnography sensor or said sidestream sampling line is physically attached to said mainstream connector or said sidestream port respectively, said hardware switching mechanism generates a flag indicative of the attached mainstream capnography sensor or sidestream sampling line, further wherein said software switching mechanism responds to said flag by notifying said controller circuit of the availability of either one of said mainstream gas values parser unit or said sidestream gas values parser unit, yet further wherein said controller circuit automatically operates said capnography module in a mainstream monitoring mode or a sidestream monitoring mode dependent upon which of said values parser units is available as indicated by said software switching mechanism; connecting said capnography module to a monitor of a patient monitoring system, said patient monitoring system further comprising a display; powering on said capnography module; connecting a mainstream capnography sensor to said capnography module; detecting said mainstream capnography sensor; delaying operation of said capnography module for a predetermined time period; switching operation of said capnography module to said mainstream monitoring mode wherein data obtained from said mainstream gas values parser unit is displayed on said display; connecting a sidestream sampling line to said capnography module, wherein said capnography module continues to operate in said mainstream monitoring mode; and, disconnecting said mainstream capnography sensor, wherein said capnography module then switches automatically to said sidestream monitoring mode.

The predetermined time period may be 10 seconds.

The present specification also discloses a method of switching automatically between mainstream monitoring and sidestream monitoring on a capnography module of a patient monitoring system, said method comprising the steps of: providing a capnography module for use with a patient monitoring system, said capnography module comprising: a monitor connector for connecting said capnography module to a monitor of said patient monitoring system, said monitor connector providing a pathway for data transmission between said capnography module and said patient monitoring system; a mainstream connector for connecting a mainstream capnography sensor to said capnography module; a sidestream port for connecting a sidestream sampling line to said capnography module; a mainstream gas values parser for analyzing data provided by a mainstream capnography sensor attached to said mainstream connector; a sidestream capnography sensor for monitoring gases provided by a sidestream sampling line attached to said sidestream port; a sidestream gas values parser for analyzing data provided by said sidestream capnography sensor; a hardware switching mechanism, comprising a plurality of circuits and communication interfaces between said circuits; a controller circuit in communication with said hardware switching mechanism and said monitor of said patient monitoring system; and, a software switching mechanism, comprising programmatic instructions stored on non-volatile memory, said software switching mechanism responsive to flags generated by said hardware switching mechanism and in communication with said controller circuit; wherein, when either one of said mainstream capnography sensor or said sidestream sampling line is physically attached to said mainstream connector or said sidestream port respectively, said hardware switching mechanism generates a flag indicative of the attached mainstream capnography sensor or sidestream sampling line, further wherein said software switching mechanism responds to said flag by notifying said controller circuit of the availability of either one of said mainstream gas values parser unit or said sidestream gas values parser unit, yet further wherein said controller circuit automatically operates said capnography module in a mainstream monitoring mode or a sidestream monitoring mode dependent upon which of said values parser units is available as indicated by said software switching mechanism; connecting said capnography module to a monitor of a patient monitoring system, said patient monitoring system further comprising a display; powering on said capnography module; connecting a sidestream sampling line to said capnography module; detecting said sidestream sampling line; delaying operation of said capnography module for a predetermined time period; switching operation of said capnography module to said sidestream monitoring mode wherein data obtained from said sidestream gas values parser unit is displayed on said display; connecting a mainstream capnography sensor to said capnography module, wherein said capnography module continues to operate in said sidestream monitoring mode; and, disconnecting said sidestream sampling line, wherein said capnography module then switches automatically to said mainstream monitoring mode.

The predetermined time period may be 10 seconds.

Optionally, the method of switching automatically between mainstream monitoring and sidestream monitoring on a capnography module of a patient monitoring system further comprises the step of reconnecting said sidestream sampling line wherein said capnography module remains in said mainstream monitoring mode indefinitely or if said sidestream sampling line is again disconnected, further wherein said capnography module switches to said sidestream monitoring mode if said mainstream capnography sensor is disconnected.

Optionally, the method of switching automatically between mainstream monitoring and sidestream monitoring on a capnography module of a patient monitoring system further comprises the step of disconnecting said mainstream capnography sensor so that said capnography module has neither a connected sidestream sampling line nor a connected mainstream capnography sensor, wherein said capnography module will not operate in either mainstream or sidestream monitoring mode and said capnography module will send said monitor a message to display on said display screen notifying a user that no sensors or sampling line is connected.

Optionally, the method of switching automatically between mainstream monitoring and sidestream monitoring on a capnography module of a patient monitoring system further comprises the steps of: connecting both a mainstream capnography sensor and a sidestream sampling line to said capnography before the step of powering on said capnography module; powering on said capnography module, wherein said capnography module will not operate in either mainstream or sidestream monitoring mode and said capnography module will send said monitor a message to display on said display screen notifying a user that both a mainstream sensor and a sidestream sampling line are connected.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 1 is an illustration of one embodiment of a capnography module having mainstream and sidestream monitoring connected to a patient;

DETAILED DESCRIPTION

Figure 2A:
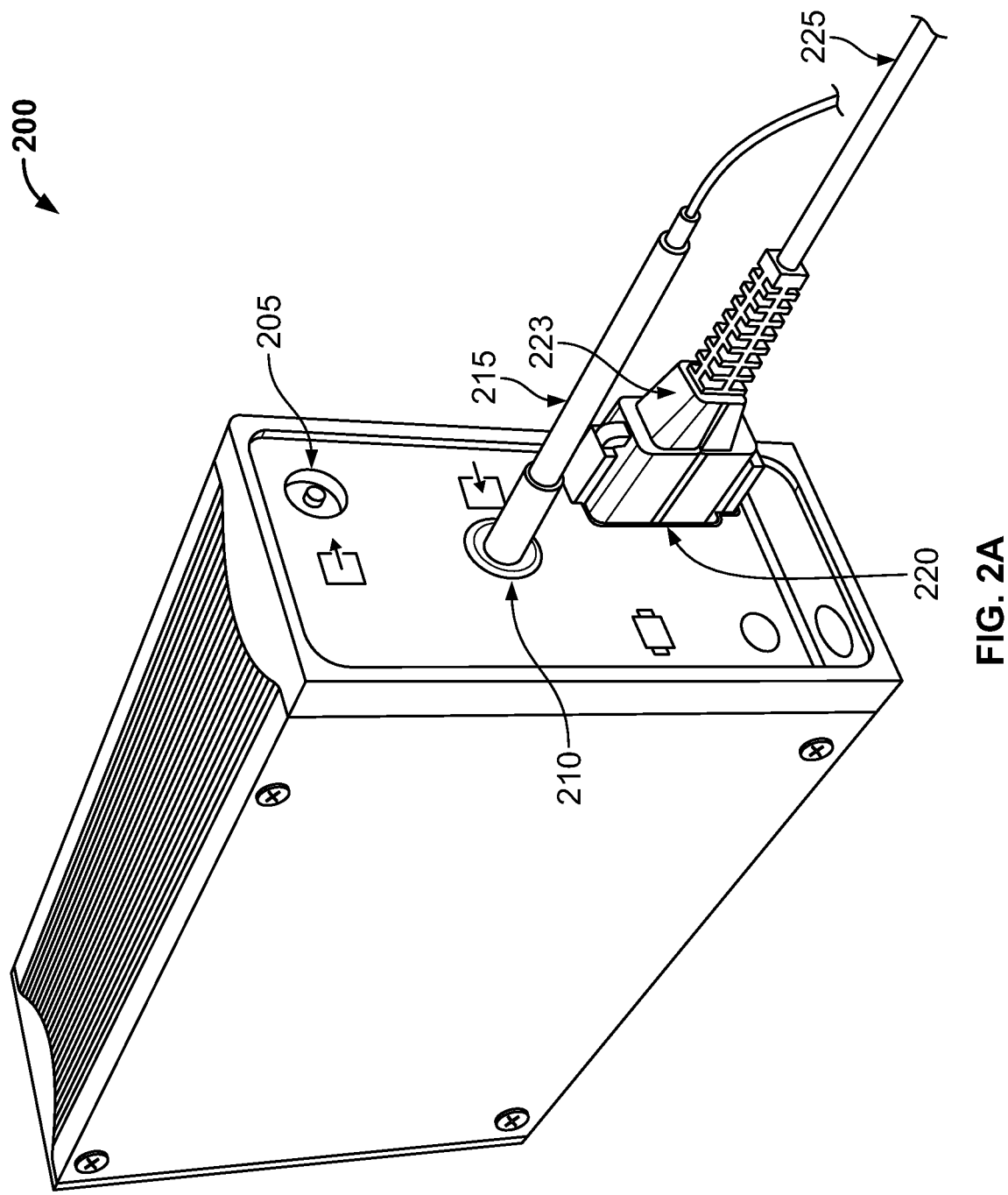
FIG. 2A is an oblique front view illustration of a capnography module in accordance with one embodiment of the present specification.

The present specification discloses a capnography module for use with a patient monitoring system wherein the capnography module is capable of switching automatically between mainstream monitoring and sidestream monitoring. The capnography module includes a switching mechanism comprising electronic hardware implementing software instructions to switch between a mainstream values parser comprising a first gas sensor and a sidestream values parser comprising a second gas sensor. The module is capable of switching automatically without removing power or rebooting the host interface capnography module. In one embodiment, both the mainstream and sidestream values parsers continually monitor $ETCO_2$, $MinCO_2$, and respiratory rate. In one embodiment, the module powers up both the mainstream and sidestream monitors, collects waveform and numeric information from both values parsers, and provides the information to the monitor of a patient monitoring system for display. The module also dispatches commands from the monitor as per an interface protocol defined within the mainstream and sidestream values parsers host interface specification. In one embodiment, a sidestream adapter is built within the module housing and a mainstream adapter is interfaced through a 9 pin connector provided in the module.

In various embodiments, the capnography module of the present specification is for use with a monitor of a patient monitoring system, such as, the monitors described in U.S. patent application Ser. No. 13/300,462, entitled "Configurable Patient Monitoring System", filed on Nov. 18, 2011 and assigned to the applicant of the present invention, and U.S. patent application Ser. No. 13/895,270, entitled "Configurable, Portable Patient Monitoring System", filed on May 15, 2013 and assigned to the applicant of the present invention, both of which are hereby incorporated by reference in their entirety. In various embodiments, the capnography module of the present specification is configured to slide into a module bay on the monitors described in the above referenced applications.

Embodiments of methods and/or devices of the present specification may involve performing or completing selected tasks manually, automatically, or a combination thereof. Some embodiments of the specification are implemented with the use of components that comprise hardware, software, firmware or combinations thereof. In some embodiments, some components are dedicated or custom components such as circuits, integrated circuits or software.

For example, in some embodiments, some of an embodiment is implemented as a plurality of software instructions executed by a data processor or computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a user interface, generally comprising one or more of input devices (e.g., allowing input of commands and/or parameters) and output devices (e.g., allowing reporting parameters of operation and results).

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is an illustration of one embodiment of a capnography module 100 having mainstream and sidestream monitoring connected to a patient 150. For mainstream monitoring, a mainstream gas sensor 121 is located in a breathing circuit. A mainstream adaptor line 125 transmits data from the mainstream gas sensor 121 to a mainstream values parser 122 located in the module 100. For sidestream monitoring, a sidestream sampling line 115 provides a gas sample to a sidestream gas sensor 111 located in the module 100. Data from the sidestream gas sensor 111 is analyzed by a sidestream values parser 112 also located in the module 100.

FIG. 2A is an oblique front view illustration of a capnography module 200 in accordance with one embodiment of the present specification. The module 200 includes a gas scavenging port 205, a sidestream sample port 210, and a mainstream connector 220. A sidestream sampling line 215 is connected to the sidestream sample port 210. A sidestream gas sensor (not shown) inside the module 200 measures the $CO_2$ content of a gas sample provided by the sidestream sampling line 215 through the sidestream sample port 210. A mainstream gas sensor (not shown) located on the breathing circuit sends measured data via a mainstream adaptor line 225 to the module 200. In one embodiment, the mainstream adaptor line 225 is connected to the mainstream connector 220 of the module 200 by a connector latching mechanism 223. The connector latching mechanism 223 is designed to secure the electrical mating connector at the proximal end of the mainstream adaptor line 225 to the mainstream connector 220 of the module 200. The connector latching mechanism 223 prevents accidental disconnection of the mainstream adaptor line 225 from the module 200.

Figure 2B:
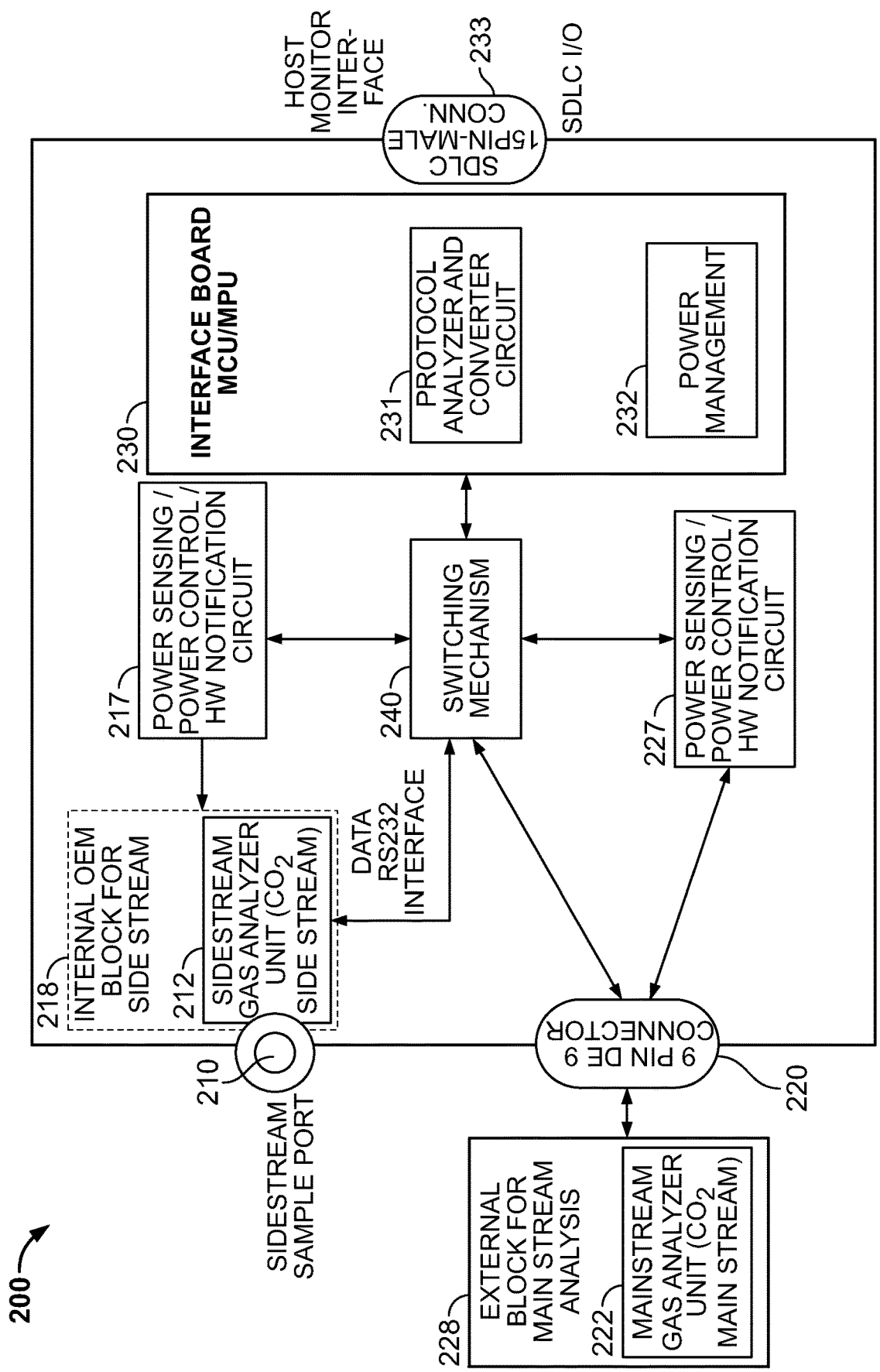
FIG. 2B is a functional block diagram of the components of a capnography module in accordance with one embodiment of the present specification.

FIG. 2B is a functional block diagram of the components of a capnography module 200 in accordance with one embodiment of the present specification. In one embodiment, the capnography module 200 includes three subunits. The subunits comprise a synchronous data link control (SDLC) interface controller board 230, a mainstream gas values parser unit 222, and a sidestream gas values parser unit 212. In one embodiment, the controller board 230 further comprises a protocol values parser and converter circuit 231 and a power management circuit 232. The controller board 230 receives patient gas data from the mainstream gas values parser unit 222 and sidestream gas values parser unit 212 via recommended standard RS-232 communication and sends this data to a monitor (not shown) of a patient monitoring system for display on a screen. The controller board 230 parses the data received from the values parsers 222, 212 and provides the decoded information to the monitor. The controller board 230 communicates with the monitor through an SDLC protocol with module power supply 15 pin male connector 233.

The controller board 230 communicates directly with a switching mechanism 240 via an RS-232 connection. The switching mechanism 240 communicates with an external block 228 used for mainstream monitoring/analysis containing the mainstream gas values parser unit 222, through a 9 pin DE-9 connector 220 via an RS-232 interface. In one embodiment, the switching mechanism 240 additionally communicates with a first power sensing/power control hardware notification circuit 227 which then communicates with the 9 pin DE-9 connector 220 via RS-232 interfaces. The mainstream gas values parser unit 222 receives sampling gas directly from an airway adaptor (not shown) from the patient. The mainstream gas values parser unit 222 analyzes the $CO_2$ content and provides the data to the controller board 230 via the switching mechanism 240 and RS-232 interfaces.

The switching mechanism 240 also communicates directly with an internal block 218 containing the sidestream gas values parser unit 212. In one embodiment, the switching mechanism 240 additionally communicates with a second power sensing/power control hardware notification circuit 217 which then communicates with the sidestream gas values parser unit 212 of the internal block 218 via RS-232 interfaces. The sidestream gas values parser unit 212 receives sampling gas from the patient through a sidestream sampling line (not shown) attached to a sidestream sample port 210. The sidestream gas values parser unit 212 measures the inspired and expired $CO_2$ levels from the patient. The sidestream gas values parser unit 212 analyzes the $CO_2$ content and provides the data to the controller board 230 via the switching mechanism 240 and RS-232 interfaces.

For all operations, the switching mechanism 240 is used to switch between the mainstream gas values parser unit 222 and the sidestream gas values parser unit 212. In one embodiment, switching between the two values parsers 222, 212 requires switching at the hardware level and at the software level.

Figure 3:
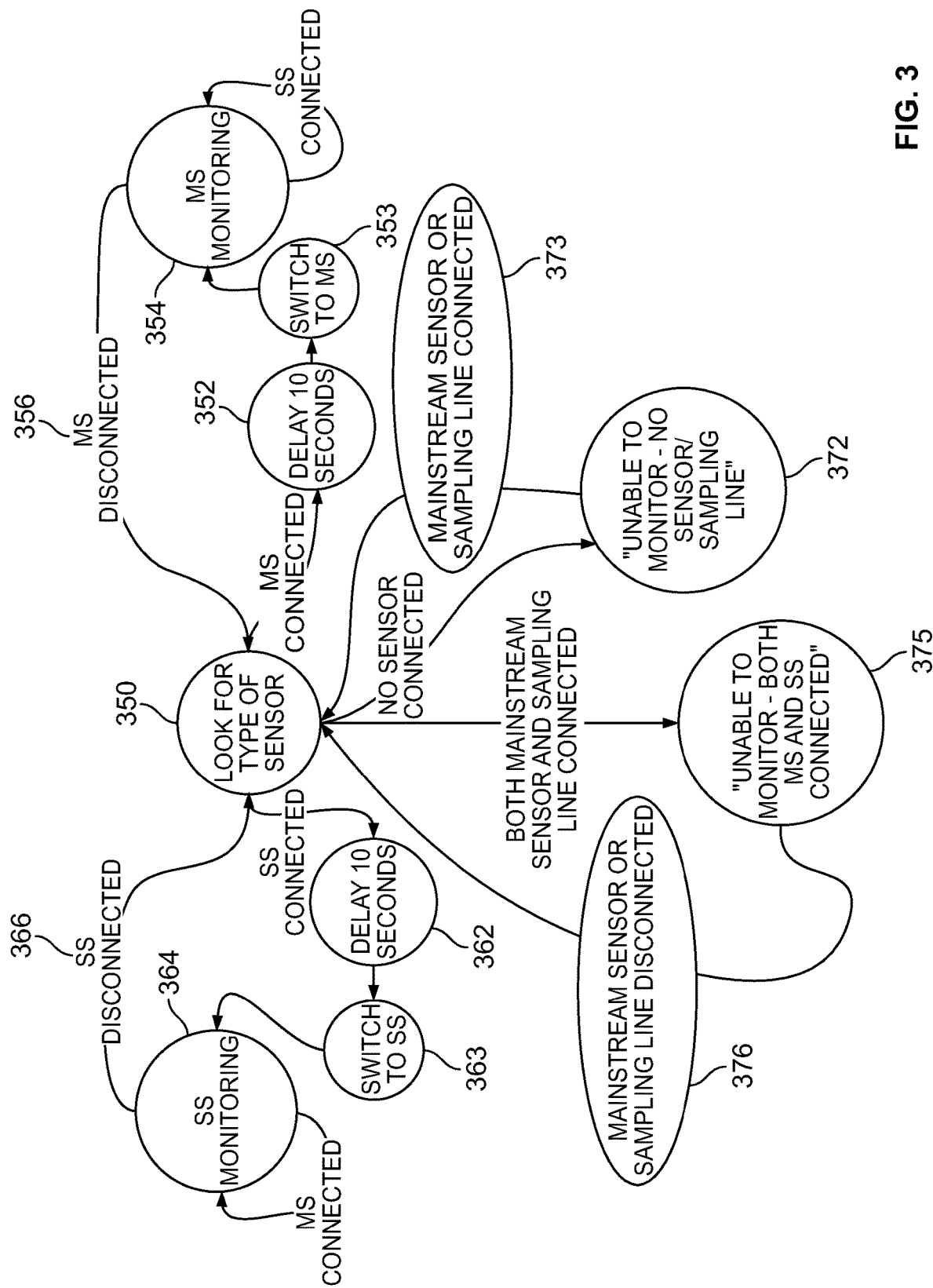
FIG. 3 is a flow diagram illustrating the steps involved in one embodiment of the software switching mechanism of the capnography module.

FIG. 3 is a flow diagram illustrating the steps involved in one embodiment of the software switching mechanism of the capnography module. At the software level, when the capnography module is first powered on, the controller board will look for the hardware availability of the mainstream and sidestream values parsers and will start an operating mode monitoring task to check if a mainstream sensor or a sidestream sampling line is attached to the module. In one embodiment, if the mainstream sensor is attached to the module, the controller board will receive a port pin PB23 'high' state from the module hardware. If the mainstream sensor is not attached to the module, the controller board will receive a port pin PB23 'low' state from the module hardware. The mainstream sensor connect and disconnect state is monitored by the monitoring task and determines which operating mode is initiated. If the mainstream sensor is connected, the module will initiate the mainstream monitoring mode. If the sidestream sampling line is connected, the module will initiate the sidestream monitoring mode. In one embodiment, the user is notified the mode currently in operation via a user interface.

Referring to FIG. 3, when the capnography module is first powered on, the controller board determines, in step 350, the type of sensor connected. If the mainstream sensor is connected and the sensor type is determined, then a 10-second delay is implemented in step 352. After the 10 second delay, the module switches, in step 353, to the mainstream gas values parser unit. The module operates, in step 354, in mainstream operating mode and continues operating in mainstream operating mode, even if a sidestream sampling line is connected. If the mainstream sensor is disconnected, in step 356, the controller board again determines the type of sensor connected in step 350.

If the sidestream sampling line is connected and the sensor type is determined, in step 350, then a 10-second delay is implemented in step 362. After the 10 second delay, the module switches, in step 363, to the sidestream gas values parser unit. The module operates, in step 364, in sidestream operating mode and continues operating in sidestream operating mode even if a mainstream sensor is connected. If the sidestream sampling line is disconnected, in step 366, the controller board again determines the type of sensor connected in step 350.

If, when the capnography module is first powered on, no sensor is connected, the controller board will recognize the absence of a sensor, no values parser or operating mode will be selected and the user interface will display "UNABLE TO MONITOR—No Sensor/Sampling Line" in step 372. If a mainstream sensor or sampling line is then connected in step 373, the controller board once again determines the type of sensor connected in step 350. If, when the capnography module is first powered on, both a mainstream sensor and a sidestream sampling line are connected, the controller board will recognize that both types of sensors are connected, no values parser or operating mode will be selected and the user interface will display "UNABLE TO MONITOR—Both MS and SS connected" in step 375. After at least one of the mainstream sensor and the sampling line is disconnected in step 376, the controller board again determines the type of sensor connected 350.

Figure 4:
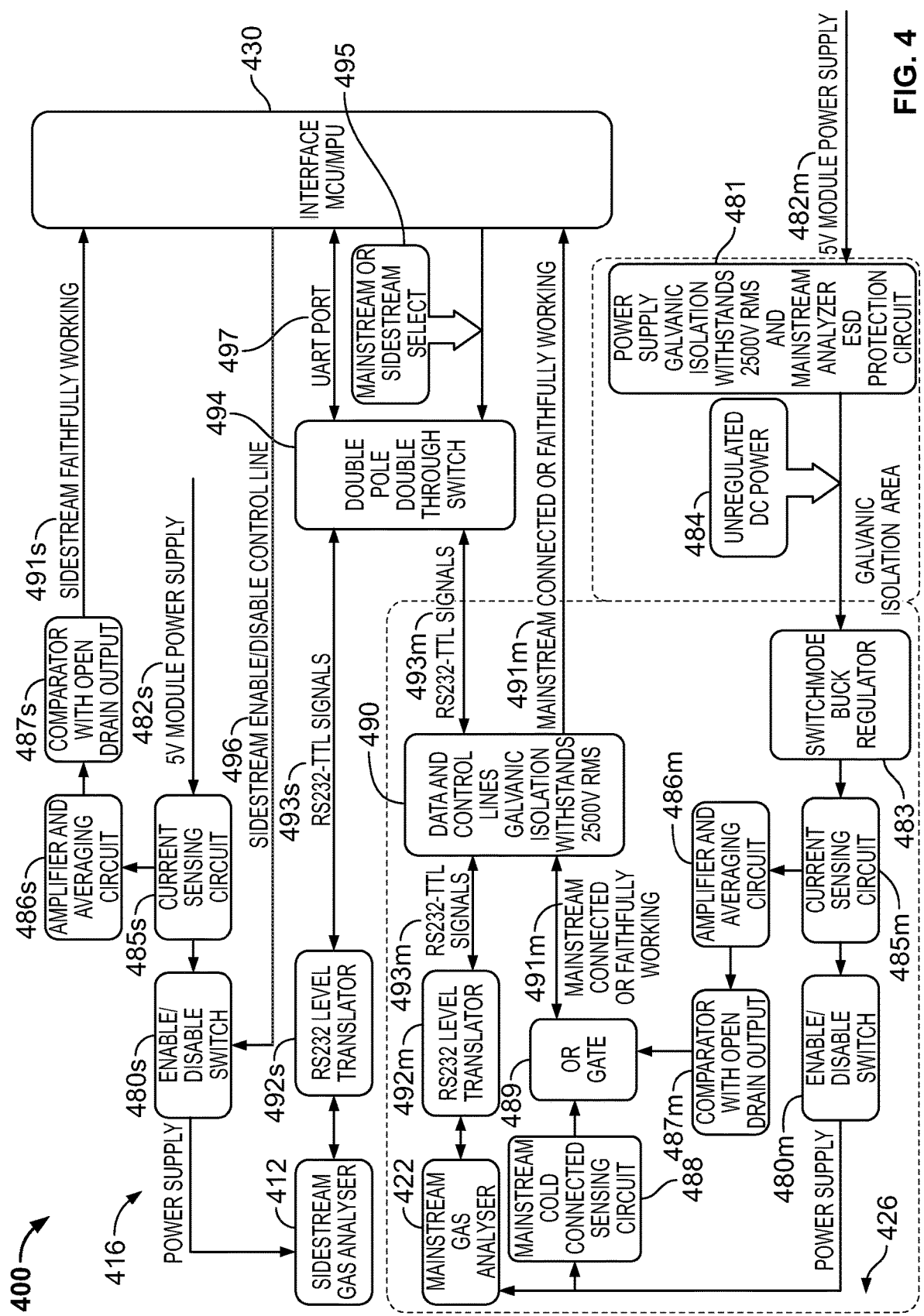
FIG. 4 is a block diagram illustrating one embodiment of the hardware switching mechanism of the capnography module.

FIG. 4 is a block diagram illustrating one embodiment of the hardware switching mechanism 400 of the capnography module. As stated previously, controller board 430 receives gas data from either a mainstream gas values parser unit 422 or a sidestream gas values parser unit 412, depending upon the operation mode of the capnography module. Automatic switching between the two values parsers 422, 412 is enabled on the module. The hardware switching mechanism 400 includes a section for mainstream monitoring 426 and another section for sidestream monitoring 416.

The mainstream monitoring section 426 includes an enable/disable switch 480m that is used to enable or disable the mainstream gas values parser unit 422 based on the operating state decided by the software as described above in conjunction with FIG. 3. In the case of the mainstream gas values parser unit 422, the control command hardware circuitry requires galvanic isolation.

A mainstream power supply galvanic isolation with electrostatic discharge (ESD) protection circuit 481 provides power and galvanic isolation, able to withstand 2500 V root means squared (RMS), to the mainstream gas values parser unit 422. The mainstream power supply galvanic isolation with electrostatic discharge (ESD) protection circuit 481 generates isolated 5 V power supply required for the mainstream gas values parser 422 from 5 V power 482m supplied by the module. The mainstream power supply galvanic isolation with electrostatic discharge (ESD) protection circuit 481 includes an isolated high frequency transformer driven by a full bridge chopper circuit with an associated secondary full wave rectifier. The full bridge metal-oxide semiconductor field-effect transistor (MOSFET) chopper circuit is driven by a dead-time controlled oscillator cum driver circuit. A high voltage, high creepage ceramic capacitor circuit is used to protect the mainstream gas values parser unit 422 from ESD. The capacitor impedes the sudden change in the isolated circuit with reference to the module's non-isolated circuit and provides a path for ESD to discharge through them, thereby protecting the mainstream gas values parser unit 422. The mainstream ESD protection circuit 481, along with the data and control lines galvanic isolation circuit 490 described below, allow the capnography module to satisfy all of the safety related tests to electromagnetic interference and electromagnetic compatibility (EMI/EMC) standards while maintaining galvanic isolation.

A switch mode buck regulator 483 is used to regulate raw unregulated DC power 484 coming from the mainstream power supply galvanic isolation with electrostatic discharge (ESD) protection circuit 481. The output of this circuit provides stable, well regulated 5 V power required for the mainstream gas values parser unit 422. A current sensing circuit 485*m* is used to measure the current flowing through the mainstream gas values parser unit 422. The current magnitude approximately indicates the health of the mainstream gas values parser unit 422. An amplifier and averaging circuit 486*m* is used to amplify the current sensing signal to the appropriate decision making level. Along with amplification, an averaging circuit is also incorporated for smoothing out any fast variations caused by the mainstream gas values parser unit's 422 runtime current consumption transients.

A comparator with open drain output 487*m* is used to notify the software switching mechanism for the availability of the mainstream gas values parser unit 422 from an electrical functionality perspective. The open drain comparator 487*m* output is used with a pull up resistor to generate a hardware flag for notifying the controller board 430 of the mainstream gas values parser unit 422 availability. A mainstream cold connected sensing circuit 488 is used to notify the software switching mechanism for appropriate action against use cases whenever a mainstream sensor is connected during runtime and when sidestream is being monitored. A standard digital OR gate 489 is used to combine the two notifications from the mainstream cold connected circuit 488 and from the comparator with open drain circuit 487*m*. The comparator 487*m* sends its output to the OR gate 489, and, in turn, to the controller board 430 to notify the controller board 430 of the functionality 'faithfulness' of the mainstream gas values parser unit 422.

A data and control lines galvanic isolation circuit 490 is used to provide the path for data and control signals 491*m* to pass between the mainstream gas values parser unit 422 and the controller board 430. The data and control lines galvanic isolation circuit 490 allows the controller board 430 to receive data from the mainstream gas values parser unit 422 and allows the controller board 430 to enable or disable the mainstream gas values parser unit 422 when not in use. In one embodiment, standard off-the-shelf isolation circuits are used to provide the desired functionality while withstanding the galvanic isolation requirements of 2500 V RMS. The data and control lines galvanic isolation circuit 490, along with the mainstream ESD protection circuit 481 described above, allow the capnography module to satisfy all of the safety related tests to electromagnetic interference and electromagnetic compatibility (EMI/EMC) standards while maintaining galvanic isolation. In one embodiment, the data and control lines galvanic isolation circuit 490 maintains electrical isolation from the host electrical system.

An RS-232 level translator 492*m* is provided on the mainstream monitoring section 426 for data reception and transmission. The controller board 430 and switching mechanism operate at 5 V standard DC power. The mainstream gas values parser unit 422 is equipped with RS-232 voltage levels for data reception and transmission. The RS-232 level translator 492*m* translates RS-232 signal levels 493*m* to standard transistor-transistor logic (TTL) signal levels. In one embodiment, the RS-232 level translator 492*m* is a standard off-the-shelf translator.

On the sidestream monitoring section 416, the hardware switching mechanism further comprises an enable/disable switch 480*s* that is used to enable or disable the sidestream gas values parser unit 412 based on the operating state decided by the software as described above. The enable/disable switch 480*s* is in communication with the controller board 430 via a sidestream enable/disable control line 496. 5 V power 482*s* is supplied to the sidestream gas values parser unit 412 by the module through a current sensing circuit 485*s*. The current sensing circuit 485*s* is used to measure the current flowing through the sidestream gas values parser unit 412. The current magnitude approximately indicates the health of the sidestream gas values parser unit 412. An amplifier and averaging circuit 486*s* is used to amplify the current sensing signal to the appropriate decision making level. Along with amplification, an averaging circuit is also incorporated for smoothing out any fast variations caused by the sidestream gas values parser unit's 412 during runtime current consumption transients.

A comparator with open drain output 487*s* is used to notify the software switching mechanism for the availability of the sidestream gas values parser unit 412 from an electrical functionality perspective. The open drain comparator 487*s* output is used with a pull up resistor to generate a hardware flag for notifying 491*s* the controller board 430 for the sidestream gas values parser unit 412 availability.

An RS-232 level translator 492*s* is provided on the sidestream monitoring section 416 for data reception and transmission. The controller board 430 and switching mechanism operate at 5 V standard DC power. The sidestream gas values parser unit 412 is equipped with RS-232 voltage levels for data reception and transmission. The RS-232 level translator 492*s* translates RS-232 signal levels 493*s* to standard TTL signal levels. In one embodiment, the RS-232 level translator 492*s* is a standard off-the-shelf translator.

A double pole double through switch 494 is used to switch controller board 430 reception and transmission data lines between the mainstream gas values parser unit 422 and the sidestream gas values parser unit 412. Low ON state resistance switches are used for avoiding any bit errors caused. The double pole double through switch 494 is in total control of the software switching mechanism based on the use cases. A universal asynchronous receiver/transmitter (UART) port 497 enables communication between the controller board 430 and the double pole double through switch 494. A mainstream or sidestream select line pin 495 is a port I/O pin from the controller board 430 under the control of the software switching mechanism that toggles the data input and output lines from the mainstream gas values parser unit 422 and the sidestream gas values parser unit 412. In one embodiment, to reduce the burden on the software switching mechanism, very few port pins are used in the microcontroller or microprocessors of the controller board 430 to enable switching between the mainstream and sidestream hardware components. The switching functionality is transferred to the enable/disable switches 480*m*, 480*s* from power/control lines 482*m*, 482*s*. The comparator with open drain output 487*m* is used to notify the microcontroller or microprocessor of the board 430 if the mainstream sensor is connected or the mainstream gas values parser unit 422 is faithfully working with the help of the OR gate 489. The comparator with open drain output 487*s* notifies the microcontroller or microprocessor of the board 430 directly when a sidestream sampling line is connected.

Figure 5:
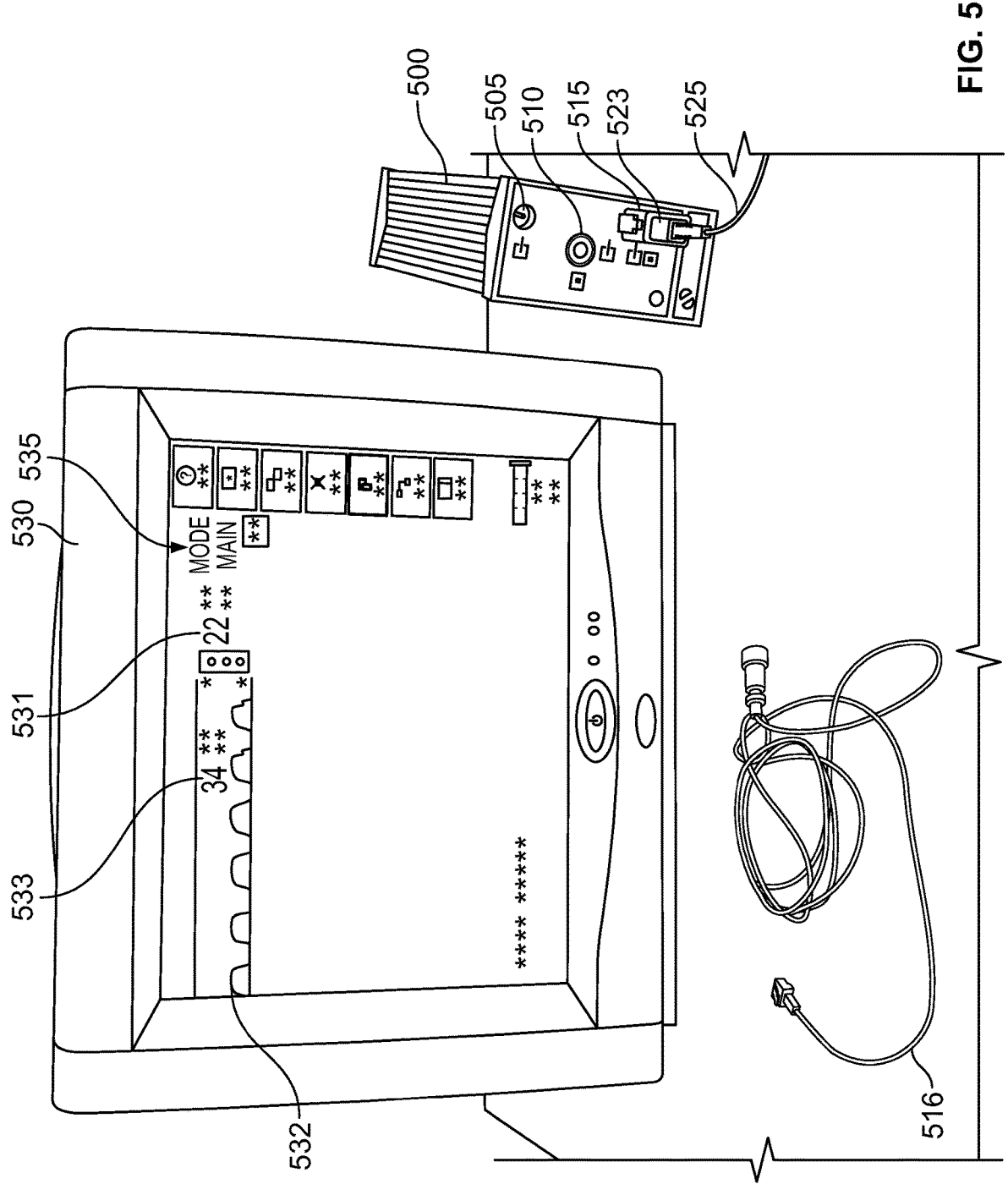
FIG. 5 is an illustration of one embodiment of a display and capnography module of a patient monitoring system, depicting a mainstream adaptor line connected to the capnography module.

FIG. 5 is an illustration of one embodiment of a display 530 and capnography module 500 of a patient monitoring system, depicting a mainstream adaptor line 525 connected to the capnography module 500. The mainstream adaptor line 525 is connected to a mainstream connector 515 on the capnography module 500 by a connector latching mechanism 523 at its proximal end. The distal end of the adaptor line 525 includes a mainstream gas sensor (not shown) that is positioned in the airway of the patient. Also depicted on the capnography module 500 are a gas scavenging port 505 and a sidestream sample port 510. The sidestream sampling line 516 is depicted unconnected in the foreground. The display 530 includes numeric 531 and waveform 532 $CO_2$ content and respiratory rate 533 information. Also included in the display 530 is the text 'MODE MAIN' 535, notifying the user that the capnography module 500 is operating in the mainstream monitoring state.

Figure 6:
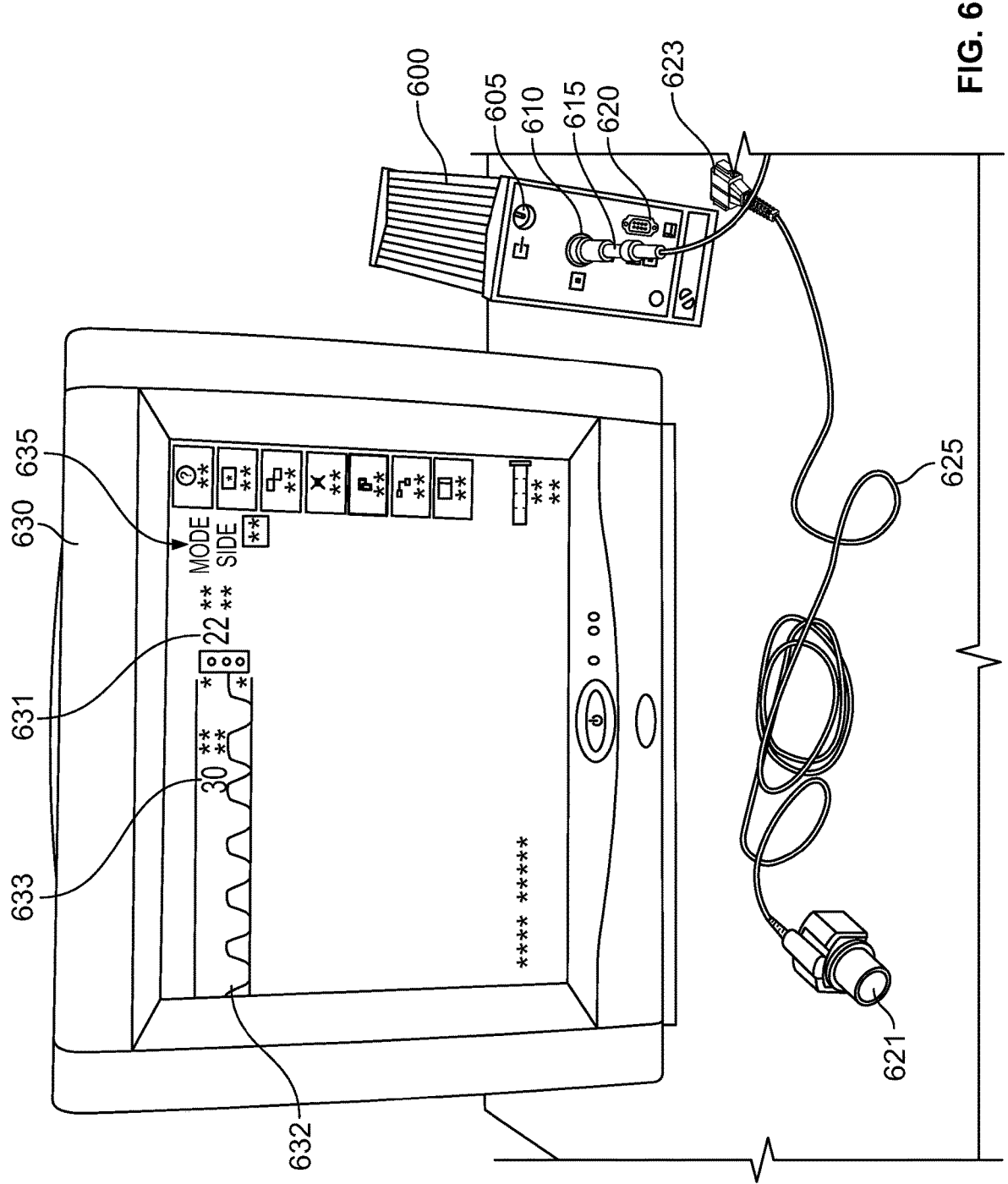
FIG. 6 is an illustration of one embodiment of a display and capnography module of a patient monitoring system, depicting a sidestream sampling line connected to the capnography module.

FIG. 6 is an illustration of one embodiment of a display 630 and capnography module 600 of a patient monitoring system, depicting a sidestream sampling line 615 connected to the capnography module 600. The sidestream sampling line 615 is connected to a sidestream sample port 610 on the capnography module 600 at its proximal end. The distal end (not shown) of the sampling line 615 takes a gas sample from the breathing circuit and provides it to a sidestream gas sensor within the capnography module 600. Also depicted on the capnography module 600 are a gas scavenging port 605 and a mainstream connector 620. The mainstream adaptor line 625 is depicted unconnected in the foreground and includes a connector latching mechanism 623 at its proximal end and a mainstream sensor 621 at its distal end. The display 630 includes numeric 631 and waveform 632 CO2 content and respiratory rate 633 information. Also included on the display is the text 'MODE SIDE' 635, notifying the user that the capnography module 600 is operating in the sidestream monitoring state.

Figure 7:
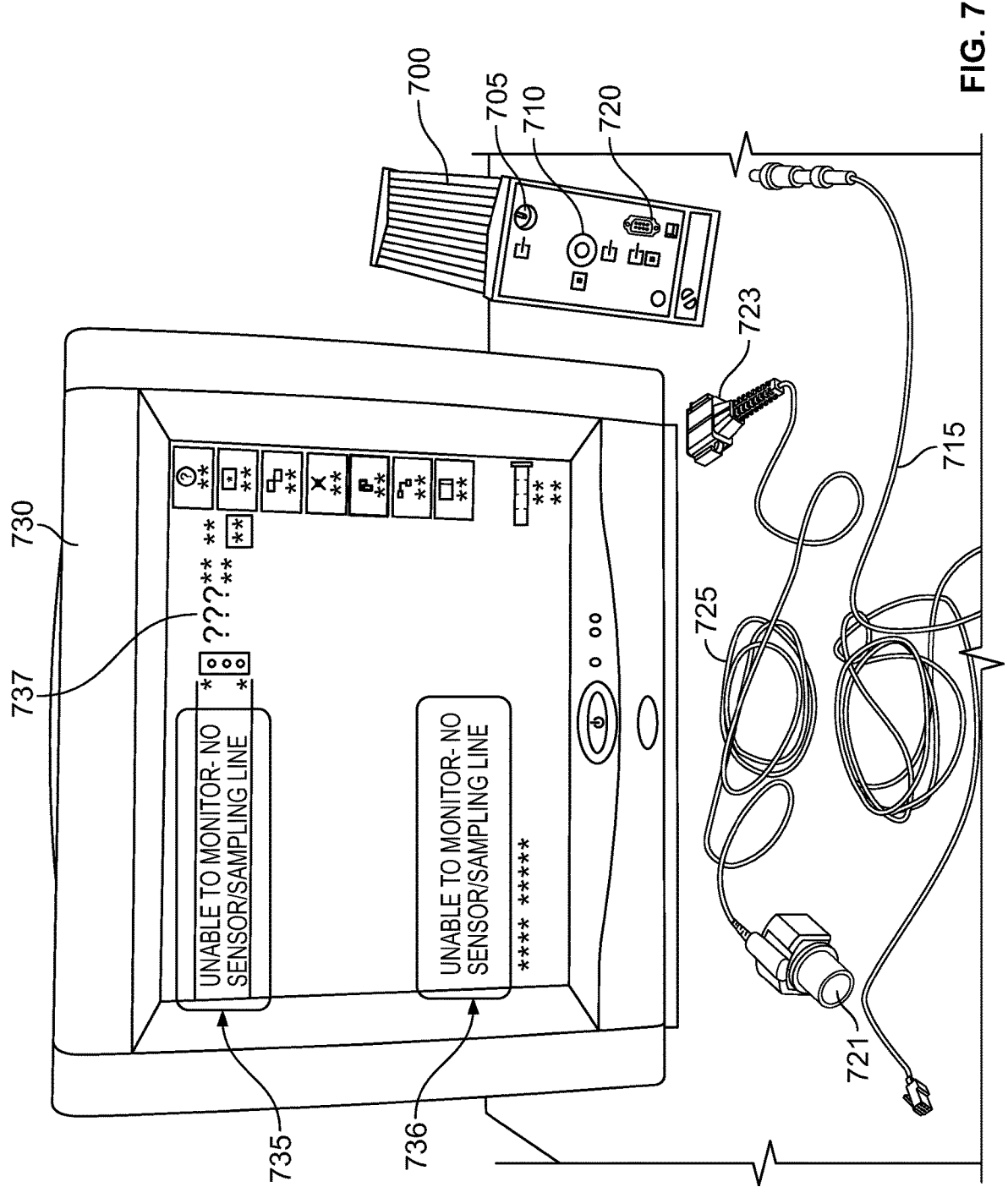
FIG. 7 is an illustration of one embodiment of a display and capnography module of a patient monitoring system, depicting no sensors connected to the capnography module; and, FIG. 8 is an illustration of one embodiment of a display and capnography module of a patient monitoring system, depicting both a mainstream adaptor line and a sidestream sampling line connected to the capnography module.

FIG. 7 is an illustration of one embodiment of a display 730 and capnography module 700 of a patient monitoring system, depicting no sensors connected to the capnography module 700. The capnography module includes a gas scavenging port 705, sidestream sample port 710, and mainstream connector 720. The mainstream adaptor line 725 is depicted unconnected in the foreground and includes a connector latching mechanism 723 at its proximal end and a mainstream sensor 721 at its distal end. The sidestream sampling line 715 is also depicted unconnected in the foreground. The display 730 includes text stating 'UNABLE TO MONITOR—No Sensor/Sampling Line' 735 in place of waveform information. In one embodiment, the text is repeated at the bottom of the screen 736. Additionally, in one embodiment, the display includes a series of questions marks '???' 737 in place of the numerical information.

The sidestream gas values parser unit is an integral part of the module and is hardwired therein. On the hardware level, the current consumed in the sidestream values parser is continuously monitored with a current sense resistor. The current data is amplified, filtered, and then sent to a comparator with a fixed reference. The comparator output is logic high (connected) or low (disconnected) and reflects the availability of the sidestream gas values parser unit. The comparator sends its output to the controller board to notify the controller board of the functionality 'faithfulness' of the sidestream gas values parser unit.

At the software level, the operating mode monitoring task will detect the non-availability of either the sidestream sensor or the mainstream sensor through the hardware inputs and the module will send the display a warning message indicating 'UNABLE TO MONITOR—No Sensor/Sampling Line' as described above. The display presents the message within a parameter display area to notify the user that no sensors are connected.

If a sidestream sensor is connected and is then subsequently disconnected, the module will send the display the same warning message indicating 'UNABLE TO MONITOR—No Sensor/Sampling line'. This message will continue to be displayed until either a mainstream sensor or a sidestream sensor is connected.

Figure 8:
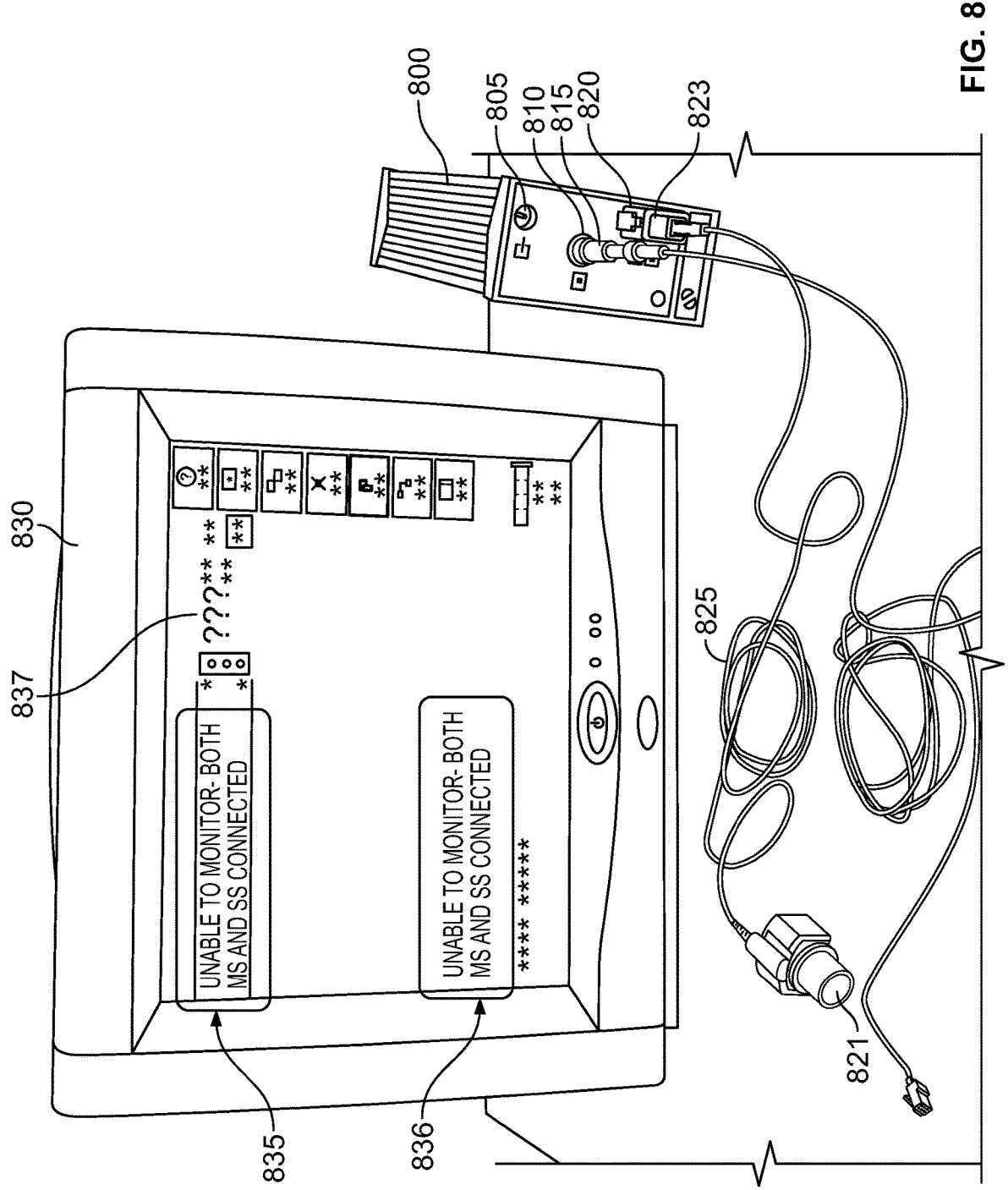

FIG. 8 is an illustration of one embodiment of a display 830 and capnography module 800 of a patient monitoring system, depicting both a mainstream adaptor line 825 and a sidestream sampling line 815 connected to the capnography module 800. The mainstream adaptor line 825 is connected to a mainstream connector 820 on the capnography module 800 by a connector latching mechanism 823 at its proximal end. The distal end of the adaptor line 825 includes a mainstream gas sensor 821 that is positioned in the airway of the patient during mainstream mode operation. The sidestream sampling line 815 is connected to a sidestream sample port 810 on the capnography module 800 at its proximal end. The distal end of the sampling line 815 takes a gas sample from the breathing circuit and provides it to a sidestream gas sensor within the capnography module 800 during sidestream mode operation. Also depicted on the capnography module 800 is a gas scavenging port 805.

If both the mainstream adaptor line 825 and the sidestream sampling line 815 are connected prior to powering on the capnography module 800, the display 830 will include text stating 'UNABLE TO MONITOR—Both MS and SS connected' 835 in place of waveform information. In one embodiment, the text is repeated at the bottom of the screen 836. Additionally, in one embodiment, the display includes a series of questions marks '???' 837 in place of the numerical information. When both sensors are connected prior to powering on the module, the hardware notifies the software switching mechanism of the inability to operate by setting hardware flags.

At the software level, the operating mode monitoring task will detect the availability of the sidestream sensor and the mainstream sensor through the hardware inputs and the module will send the display a warning message indicating 'UNABLE TO MONITOR—Both MS and SS connected' as described above. The display presents the message within a parameter display area to notify the user that both sensors are connected.

In another embodiment, when both sensors are connected during runtime, the capnography module continues to monitor in the current mode. The hardware sends a notification to the software switching mechanism by setting hardware flags. At the software level, if, during sidestream monitoring, a mainstream sensor is connected, the module will continue to monitor in the sidestream monitoring mode. When the user disconnects the sidestream sampling line, then the software switching mechanism will switch the module to mainstream monitoring.

In another embodiment, when the mainstream sensor is connected while the capnography module is monitoring the sidestream, the mainstream cold connected sensing circuit (hardware level) detects the condition and does not energize the mainstream values parser. The mainstream cold connected sensing circuit then notifies the software switching mechanism to take appropriate action based on the use case. At the software level, unless the sidestream sampling line is removed, the software switching mechanism will not cause the module to switch to mainstream monitoring and the module will continue to monitor in sidestream mode. In other words, when a mainstream sensor is connected, the software switching mechanism receives motivation from the hardware. The software switching mechanism periodically polls the hardware flag to determine the appropriate switching action based on use case.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of switching automatically between mainstream monitoring and sidestream monitoring in a capnography module of a patient monitoring system, said method comprising the steps of:
providing a capnography module configured to be used with a patient monitoring system, wherein said capnography module comprises:
a monitor connector configured to connect said capnography module to a monitor of the patient monitoring system, wherein said monitor includes a display screen;
a mainstream connector configured to connect a mainstream capnography sensor to said capnography module;
a sidestream port configured to connect a sidestream sampling line to said capnography module;
a mainstream gas values parser unit configured to analyze data provided by a mainstream capnography sensor attached to said mainstream connector;
a sidestream capnography sensor configured to monitor gases provided by a sidestream sampling line attached to said sidestream port;
a sidestream gas values parser unit configured to analyze data provided by said sidestream capnography sensor;
a hardware switching mechanism, comprising a plurality of circuits and communication interfaces between said circuits, wherein the hardware switching mechanism is configured to generate a flag indicative of the attached mainstream capnography sensor or sidestream sampling line when either one of the mainstream capnography sensor or the sidestream sampling line is physically attached to the mainstream connector or the sidestream port respectively;
a controller circuit in communication with said hardware switching mechanism and said monitor of said patient monitoring system; and
a software switching mechanism, comprising programmatic instructions stored on non-volatile memory, said software switching mechanism responsive to flags generated by said hardware switching mechanism and in communication with said controller circuit, wherein the software switching mechanism is configured to respond to the flag by notifying the controller circuit of the availability of either one of the mainstream gas values parser unit or the sidestream gas values parser unit and wherein the controller circuit is configured to automatically operate the capnography module in a mainstream monitoring mode or a sidestream monitoring mode dependent upon which of the values parser units is available as indicated by said software switching mechanism;
connecting said capnography module to the monitor of said patient monitoring system;
powering on said capnography module;
connecting a sidestream sampling line to said capnography module;
detecting said sidestream sampling line;
delaying operation of said capnography module for a predetermined time period;
switching operation of said capnography module to said sidestream monitoring mode wherein data obtained from said sidestream gas values parser unit is displayed on said display;
connecting a mainstream capnography sensor to said capnography module, wherein said capnography module continues to operate in said sidestream monitoring mode; and,
disconnecting said sidestream sampling line, wherein said capnography module then switches automatically to said mainstream monitoring mode.

2. The method of claim 1, wherein said predetermined time period is 10 seconds.

3. The method of claim 1, further comprising reconnecting said sidestream sampling line wherein, after reconnecting the sidestream sampling line, said capnography module remains in said mainstream monitoring mode.

4. The method of claim 1, further comprising disconnecting said mainstream capnography sensor so that said capnography module has neither a connected sidestream sampling line nor a connected mainstream capnography sensor, wherein said capnography module will not operate in either mainstream or sidestream monitoring mode and said capnography module will send said monitor a message to display on said display screen notifying a user that no sensors or sampling line is connected.

5. The method of claim 1, wherein the hardware switching mechanism comprises a power supply galvanic isolation circuit to protect the mainstream gas values parser unit from electrostatic discharge.

6. The method of claim 5, wherein the hardware switching mechanism further comprises a switch mode buck regulator for regulating DC power from the power supply galvanic isolation circuit and providing regulated power to the mainstream gas values parser unit.

7. The method of claim 1, wherein the hardware switching mechanism comprises a data and control line galvanic isolation circuit to protect the mainstream gas values parser unit from electrostatic discharge.

8. The method of claim 1, wherein the hardware switching mechanism further comprises a current sensing circuit, an amplifier and averaging circuit, and a comparator for the mainstream gas values parser unit.

9. The method of claim 1, wherein the hardware switching mechanism further comprises a current sensing circuit, an amplifier and averaging circuit, and a comparator for the sidestream gas values parser unit.

10. The method of claim 1, further comprising monitoring an increase in a current level for the mainstream gas values parser unit or the sidestream gas values parser unit when the mainstream capnography sensor or the sidestream sampling line is connected to the capnography module.

11. The method of claim 10, further comprising notifying the controller circuit of the availability of the mainstream gas values parser unit when the current level of the mainstream gas values parser unit has increased, indicating a connection to the mainstream capnography sensor.

12. The method of claim 10, further comprising notifying the controller circuit of the availability of the sidestream gas values parser unit when the current level of the sidestream gas values parser unit has increased, indicating a connection to the sidestream sampling line.

13. The method of claim 1, wherein the hardware switching mechanism further comprises an OR gate for receiving signals from a sensing circuit and a comparator for the mainstream gas values parser, wherein the OR gate is configured to determine if the mainstream gas values parser is available based upon said signals received from the sensing circuit.

14. The method of claim 1, wherein the mainstream gas values parser is equipped with a RS-232 voltage level for data reception and transmission.

15. The method of claim 14, wherein the hardware switching mechanism comprises a RS-232 level translator for translating the RS-232 voltage level of the mainstream gas values parser unit to a transistor-transistor logic signal level.

16. The method of claim 1, wherein the sidestream gas values parser is equipped with a RS-232 voltage level for data reception and transmission.

17. The method of claim 16, wherein the hardware switching mechanism comprises a RS-232 level translator for translating the RS-232 voltage level of the sidestream gas values parser unit to a transistor-transistor logic signal level.

* * * * *